US010653460B2

(12) United States Patent
Jackson

(10) Patent No.: US 10,653,460 B2
(45) Date of Patent: May 19, 2020

(54) ORTHOPEDIC IMPLANT ROD REDUCTION TOOL SET AND METHOD

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 16/355,103

(22) Filed: Mar. 15, 2019

(65) Prior Publication Data

US 2019/0209217 A1 Jul. 11, 2019

Related U.S. Application Data

(63) Continuation of application No. 16/028,796, filed on Jul. 6, 2018, now Pat. No. 10,258,391, which is a continuation of application No. 15/897,377, filed on Feb. 15, 2018, now abandoned, which is a continuation of application No. 15/481,192, filed on Apr. 6, 2017, now Pat. No. 9,924,982, which is a continuation of application No. 14/733,222, filed on Jun. 8, 2015, now Pat. No. 9,636,151, which is a continuation of application No. 13/815,933, filed on Mar. 15, 2013, now Pat. No. 9,050,139.

(51) Int. Cl.
*A61B 17/70* (2006.01)
*A61B 17/56* (2006.01)

(52) U.S. Cl.
CPC ...... *A61B 17/7085* (2013.01); *A61B 17/7001* (2013.01); *A61B 17/7002* (2013.01); *A61B 17/7011* (2013.01); *A61B 17/7032* (2013.01); *A61B 17/7035* (2013.01); *A61B 17/7037* (2013.01); *A61B 17/7076* (2013.01); *A61B 17/7082* (2013.01); *A61B 17/7086* (2013.01); *A61B 17/7088* (2013.01); *A61B 17/7089* (2013.01); *A61B 17/7091* (2013.01); *A61B 2017/564* (2013.01)

(58) Field of Classification Search
CPC ........... A61B 17/7085; A61B 17/7001; A61B 17/7002; A61B 17/7011; A61B 17/7032; A61B 17/7035; A61B 17/7037; A61B 17/7086; A61B 17/7088; A61B 17/7091; A61B 2017/564
USPC ........................... 606/86 A, 60, 78, 246–279
See application file for complete search history.

(56) References Cited

U.S. PATENT DOCUMENTS

| | | | |
|---|---|---|---|
| 854,956 | A | 5/1907 | Martin |
| 2,243,717 | A | 5/1941 | Godoy et al. |
| 2,524,095 | A | 10/1950 | Williams |
| 2,531,892 | A | 11/1950 | Reese |
| 2,532,972 | A | 12/1950 | Vertin |
| 2,579,438 | A | 12/1951 | Longfellow |
| 2,669,896 | A | 2/1954 | Clough |
| 2,813,450 | A | 11/1957 | Dzus |
| 3,013,244 | A | 12/1961 | Rudy |
| 3,236,275 | A | 2/1966 | Smith |

(Continued)

FOREIGN PATENT DOCUMENTS

| | | |
|---|---|---|
| DE | 20207850 | 10/2002 |
| WO | WO 95/013755 | 5/1995 |

OTHER PUBLICATIONS

European Search Report, EP14189707.4, dated Feb. 25, 2015.

*Primary Examiner* — Pedro Philogene
(74) *Attorney, Agent, or Firm* — Polsinelli PC

(57) ABSTRACT

A tool set for implanting a rod in a human spine in conjunction with bone screws.

9 Claims, 17 Drawing Sheets

(56) References Cited

U.S. PATENT DOCUMENTS 4,269,178 A 5/1981 Keene
5,020,519 A 6/1991 Hayes
D346,217 S 4/1994 Sparker
5,443,467 A 8/1995 Biedermann et al.
5,961,517 A 10/1999 Biedermann et al.
6,077,262 A 6/2000 Schlapfer et al.
6,139,549 A 10/2000 Keller
6,183,472 B1 2/2001 Lutz
6,214,012 B1 4/2001 Karpman et al.
6,273,888 B1 8/2001 Justis
6,280,442 B1 8/2001 Barker et al.
6,287,311 B1 9/2001 Sherman et al.
6,302,888 B1 10/2001 Mellinger et al.
6,440,133 B1 8/2002 Beale et al.
6,488,681 B2 12/2002 Martin et al.
6,530,929 B1 3/2003 Justis et al.
6,540,749 B2 * 4/2003 Schafer ................ A61B 17/701 606/265
6,565,565 B1 5/2003 Yuan et al.
6,648,888 B1 * 11/2003 Shluzas .............. A61B 17/7086 606/86 A
6,730,089 B2 5/2004 Jackson
6,755,829 B1 6/2004 Bono et al.
6,837,889 B2 1/2005 Shluzas
6,911,030 B1 6/2005 Vanacker et al.
6,932,822 B2 8/2005 Oribe et al.
7,066,937 B2 6/2006 Shluzas
7,087,057 B2 8/2006 Konieczynski et al.
7,090,679 B2 8/2006 Saint-Martin et al.
7,144,396 B2 12/2006 Shluzas
7,160,300 B2 1/2007 Jackson
7,250,052 B2 7/2007 Landry et al.
7,377,923 B2 5/2008 Purcell et al.
7,527,638 B2 5/2009 Anderson et al.
7,547,318 B2 6/2009 Birkmeyer et al.
7,618,444 B2 11/2009 Shluzas
7,666,188 B2 2/2010 Anderson et al.
7,686,835 B2 3/2010 Warnick
7,708,763 B2 5/2010 Selover et al.
7,722,651 B2 5/2010 Kwak et al.
7,862,587 B2 1/2011 Jackson
7,951,172 B2 5/2011 Chao et al.
7,985,242 B2 7/2011 Forton et al.
8,034,084 B2 10/2011 Landry et al.
8,043,343 B2 10/2011 Miller et al.
8,048,129 B2 11/2011 Forton et al.
8,066,739 B2 11/2011 Jackson
8,075,592 B2 12/2011 Landry et al.
8,100,915 B2 1/2012 Jackson
8,100,946 B2 1/2012 Strasbaugh et al.
8,133,262 B2 3/2012 Whipple
8,162,948 B2 4/2012 Jackson
8,262,704 B2 9/2012 Matthis et al.
8,377,067 B2 2/2013 Jackson
8,430,914 B2 4/2013 Spratt et al.
8,894,655 B2 11/2014 Fallin et al.
9,050,148 B2 6/2015 Jackson
9,055,978 B2 6/2015 Jackson
9,101,415 B2 8/2015 Jackson
9,173,682 B2 11/2015 Jackson
9,192,413 B2 11/2015 Biedermann et al.
9,198,698 B1 12/2015 Doose et al.
9,216,039 B2 12/2015 Jackson
9,265,534 B2 2/2016 Jackson
9,265,535 B2 2/2016 Jackson
9,265,536 B2 2/2016 Jackson
9,265,537 B2 2/2016 Jackson
9,271,767 B2 3/2016 Jackson
9,532,815 B2 1/2017 Jackson
9,585,701 B2 3/2017 Jackson
9,636,151 B2 5/2017 Jackson
9,662,143 B2 5/2017 Jackson
9,662,151 B2 5/2017 Jackson
9,788,868 B2 10/2017 Jackson
9,918,751 B2 3/2018 Jackson
9,924,982 B2 3/2018 Jackson
10,039,571 B2 8/2018 Jackson
10,166,049 B2 1/2019 Jackson
2002/0026193 A1 2/2002 Barker et al.
2002/0035366 A1 3/2002 Walder et al.
2002/0091386 A1 7/2002 Martin et al.
2002/0116001 A1 8/2002 Schafer et al.
2002/0133154 A1 9/2002 Saint-Martin
2002/0143341 A1 10/2002 Biedermann et al.
2003/0023240 A1 1/2003 Amrein et al.
2003/0100904 A1 5/2003 Biedermann
2004/0143265 A1 7/2004 Landry et al.
2004/0167525 A1 8/2004 Jackson
2004/0172022 A1 9/2004 Landry et al.
2005/0131408 A1 6/2005 Sicvol et al.
2005/0149036 A1 7/2005 Varieur et al.
2005/0192573 A1 9/2005 Abdelgany et al.
2005/0216003 A1 9/2005 Biedermann et al.
2006/0036252 A1 2/2006 Baynham et al.
2006/0079909 A1 4/2006 Runco
2006/0173454 A1 8/2006 Spitler et al.
2006/0247658 A1 11/2006 Pond, Jr. et al.
2006/0293693 A1 12/2006 Farr et al.
2007/0055241 A1 3/2007 Matthis et al.
2008/0161857 A1 7/2008 Hestad et al.
2008/0172062 A1 7/2008 Donahue et al.
2008/0228228 A1 9/2008 Hestad et al.
2009/0105769 A1 4/2009 Rock et al.
2009/0198281 A1 8/2009 Rice et al.
2009/0204155 A1 8/2009 Aschmann
2010/0036426 A1 2/2010 Mitchell
2011/0015678 A1 1/2011 Jackson
2011/0060344 A1 * 3/2011 Sicvol ................ A61B 17/7032 606/104
2011/0152947 A1 * 6/2011 Kirschman ........ A61B 17/7032 606/302
2012/0071886 A1 3/2012 Jackson
2013/0197586 A1 * 8/2013 Matthis .............. A61B 17/7035 606/278
2015/0080974 A1 3/2015 Jackson
2015/0142060 A1 5/2015 Jackson
2016/0015433 A1 1/2016 Jackson
2017/0181775 A1 6/2017 Jackson
2018/0132910 A1 5/2018 Jackson
2018/0146991 A1 5/2018 Jackson
2018/0168702 A1 6/2018 Jackson
2018/0310968 A1 11/2018 Jackson
2018/0325559 A1 11/2018 Jackson
2018/0344358 A1 12/2018 Jackson
2019/0090918 A1 3/2019 Jackson
2019/0209218 A1 7/2019 Jackson
2019/0247095 A1 8/2019 Jackson

* cited by examiner

16/17

ORTHOPEDIC IMPLANT ROD REDUCTION TOOL SET AND METHOD

CROSS-REFERENCE TO RELATED APPLICATION

This application is a continuation of U.S. application Ser. No. 16/028,796 filed Jul. 6, 2018, which is a continuation of U.S. application Ser. No. 15/897,377 filed Feb. 15, 2018, now abandoned, which is a continuation of U.S. application Ser. No. 15/481,192 filed Apr. 6, 2017, now U.S. Pat. No. 9,924,982, which is a continuation of U.S. application Ser. No. 14/733,222 filed Jun. 8, 2015, now U.S. Pat. No. 9,636,151, which is a continuation of U.S. application Ser. No. 13/815,933 filed Mar. 15, 2013, now U.S. Pat. No. 9,050,139 all of which are fully incorporated herein for all purposes.

BACKGROUND OF THE INVENTION

The present invention relates to apparatuses and methods for use in performing spinal surgery and, in particular, to tools and methods of using such tools, especially for percutaneously implanting a rod for spinal support and alignment using minimally invasive techniques.

For many years, spinal osteosynthesis apparatuses have been utilized to correct spinal deformities, injuries or disease. In such procedures, elongate rods are surgically attached to vertebrae of the spine to provide support and/or to reposition certain vertebrae. Such rods are secured to vertebrae utilizing bone screws and other implants.

Surgical techniques and bone screws have improved; however, in order to reduce the impact of such surgery on the patient, it has been desirable for such implants to be inserted percutaneously or with surgical techniques that are minimally invasive to the body of the patient. This presents a problem with implantation of rods that are elongate and have historically required a long incision and open wound in order to provide for the length of the rod and the space required for the surgeon's hands to manipulate the rod, implants and insertion tools used with the rod. Consequently, it has been desirable to develop apparatuses and techniques that allow for the insertion of bone screws, the insertion and reduction of a rod and the securing of the rod to the bone screws with significantly reduced invasion into the body of the patient and with minimal incision size in the skin over the operational site.

SUMMARY OF THE INVENTION

In a first embodiment an elongate guide tool in combination with a spinal bone screw implant are provided. The guide tool is reversibly attachable to the bone screw and is useful for guiding a rod into a receiver of the bone screw during a minimally invasive percutaneous surgical procedure. The guide tool includes a body with a longitudinally extending through-bore that extends from a top opening to a bottom opening. The through-bore is sized and shaped for receiving a closure top therethrough. The guide tool also includes a laterally extending pass-through slot that extends upwardly from the body bottom opening and is joined with the through-bore. The guide tool body includes upper, middle and lower portions and the pass-through slot extends from the lower portion toward the middle portion.

The pass-through slot defines a pair of spaced opposed legs and is sized and shaped so as to receive a rod therethrough. The pass-through slot is alignable with a U-shaped channel of the bone screw upon rotation attachment of the guide tool onto the bone screw. The guide tool also includes a first attachment structure that is sized and shaped to cooperatively engage a second attachment structure of the bone screw when the guide tool is secured to the bone screw. The first and second attachment structures are complementary in size and shape. Additionally, when the pass-through slot and the U-shaped channel are aligned, the rod is transferable from the guide tool to the bone screw.

In a further embodiment, the guide tool also includes a cutout or relief portion that is sized, shaped and positioned so as to straddle a rod installed in the bone screw U-shaped channel when the guide tool is rotated such that the pass-through slot and the U-shaped channel are not aligned.

In another further embodiment, each of the legs includes an inner surface that includes the first attachment structure. The guide tool first attachment structure reversibly engages the bone screw second attachment structure upon rotation of the guide tool relative to a head of the bone screw. The first and second attachment structures cooperate so as to substantially align the guide tool pass-through slot and the bone screw U-shaped channel such that the rod is transferable therebetween. Each of the leg inner surfaces may also include a portion of a guide and advancement structure thereon.

In yet another further embodiment, the first attachment structure includes an off-set detent sized and shaped so as to be cooperatively rotatably received by the bone screw second attachment structure. Accordingly, the bone screw second attachment structure is an off-axis partially circumferential slot sized and shaped to reversibly engage the off-set detent.

In another further embodiment, the first attachment structure includes an off-set cam sized and shaped so as to be cooperatively rotatably received by the bone screw second attachment structure. Accordingly, the bone screw second attachment structure is a camming groove or slot sized and shaped to reversibly engage the off-set cam.

In still another further embodiment, the first attachment structure includes an inwardly extending shelf near the guide tool bottom opening, the shelf being sized and shaped so as to be cooperatively rotatably engage the bone screw second attachment structure. Accordingly, the bone screw second attachment structure is a partially circumferential, slot or notch sized and shaped to rotatably receive the shelf therein.

In some embodiments, each of the guide tool legs includes a recessed radially extending pin-receiving bore joining an inner surface of the leg with an outer surface of the body. The pin-receiving bores are opposed to one another. The guide tool also includes an engagement member attached to the body and which has a pair of longitudinally extending inwardly biased tangs. Each of the tangs includes an inwardly extending lower engagement pin sized, shaped and located so as to reversibly extend through a respective pin-receiving bore and reversibly engage a bone screw second attachment structure. The pin-receiving bores are substantially coaxial. In some further embodiments, each of the legs further includes a bottom ridge sized and shaped for reversible engagement by a cooperatively shaped bone screw second attachment structure.

The drawings constitute a part of this specification and include exemplary embodiments of the present invention and illustrate various objects and features thereof.

DETAILED DESCRIPTION OF THE INVENTION

Figure 1:
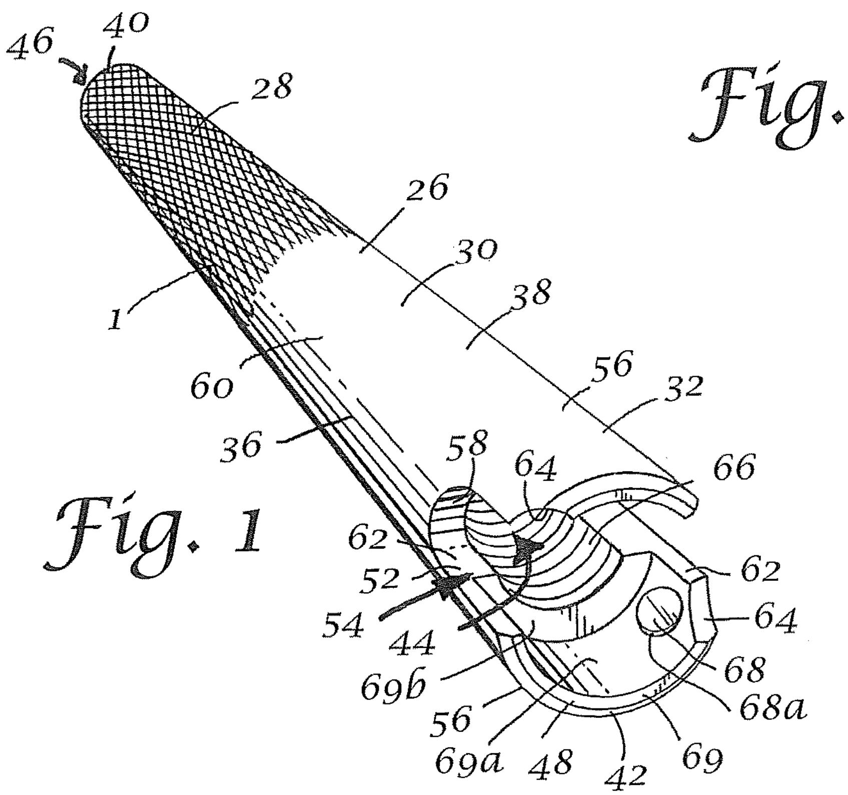
FIG. 1 is perspective view of a guide tool for percutaneously implanting a rod in a patient, in a first embodiment.
Figure 2:
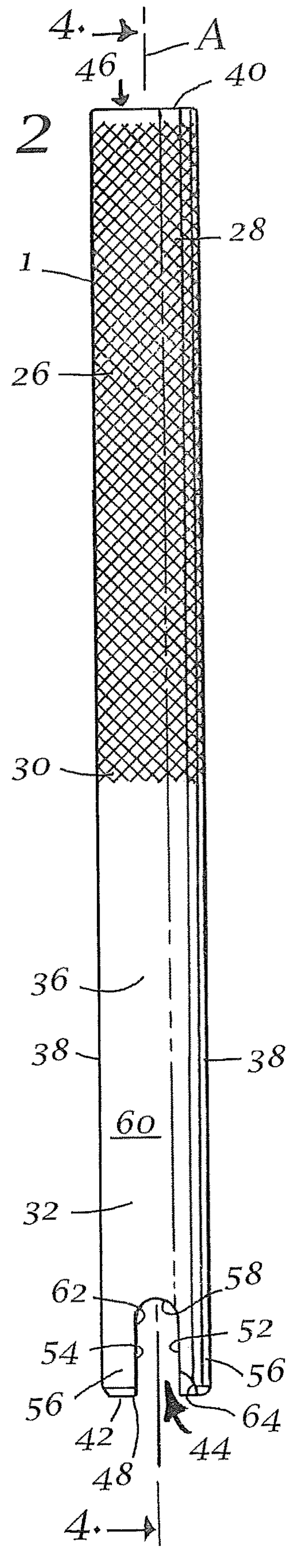
FIG. 2 is a reduced side view of the guide tool of FIG. 1.
Figure 3:
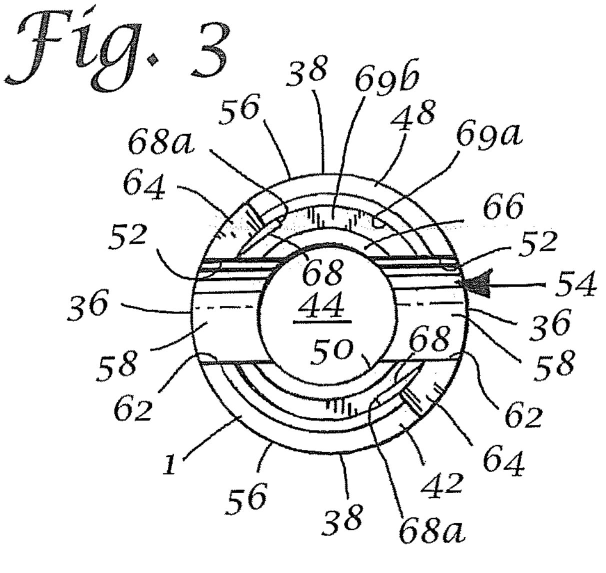
FIG. 3 is an enlarged bottom view of the guide tool of FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

FIGS. 1-25 illustrate a first embodiment of a guide tool, denoted by the numeral 100, for use in installing an orthopedic spinal rod 4 into a bone screw 6 in accordance with the present invention. The guide tool 1 is generally one of a plurality of such tools in a set of tools for installing the rod 4 into several bone screws 6. Depending upon the particular application, the tool set may include none, one or many guide tools 1 of the present invention in addition to none, one or many additional alternative tools (not shown), such as but not limited to intermediate and end guide tools, rod pushers, anti-torque tools, drivers, and the like, such as are described in U.S. Pat. Nos. 7,160,300, 7,651,502, 7,621,918, 7,862,587, 8,066,739, 8,100,915, 8,152,810, each of which is incorporated by reference herein in its entirety. The bone screws and guide tool are adapted to be used together and have complementary mating structures by which to be engaged and reversibly locked together. The bone screws 6 are implanted in the patent's spine and, in particular, in vertebrae 8 along the spine. Rods 4 are often installed on both sides of the spine, as is known in the art, during the same procedure.

With reference to FIGS. 5-25 and referring more specifically to the bone screw 6, each of the bone screws 6 includes a threaded shank 10 for screwing into and seating in a vertebra 8 that is part of the human spine, such as is known in the art. Each of the bone screws 6 also include a head 12, or receiver, with a pair of upstanding arms that have top surfaces 15 and define a rod receiving U-shaped channel 16 passing therethrough. The shank 10 may include an optional longitudinally extending cannula 11 that is sized and shaped to receive a guide wire or pin 11*a* therethrough to aid in implantation of the bone screw 6, such as is known in the art.

Figure 11:
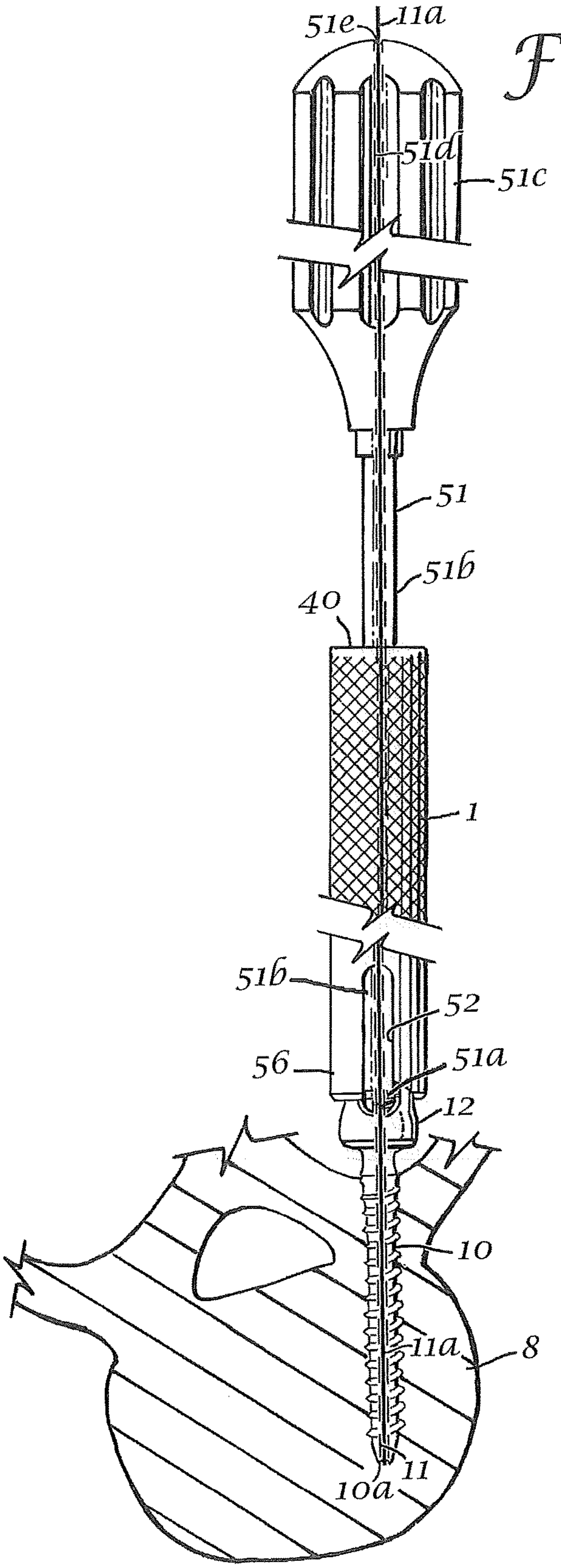
FIG. 11 is a side view of the tool of FIG. 2 with an attached polyaxial bone screw illustrating driving the bone screw into a vertebra using a bone screw driver adapted for use with the bone screw and the guide tool and also showing, in phantom, a guide wire extending upwardly through a cannula in the bone screw and through a cannula in the bone screw driver.
Figure 12:
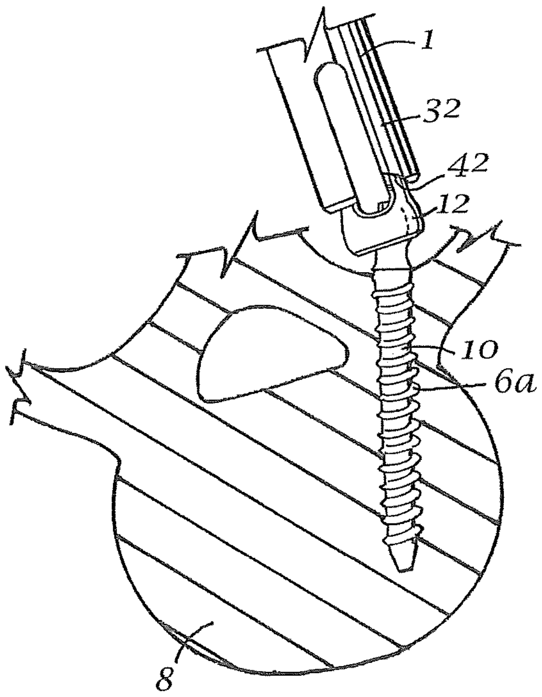
FIG. 12 is a side view of the guide tool of FIG. 11, with portions broken away and after the bone screw driver has been removed, illustrating use of the guide tool to adjust the position of the bone screw head relative to the bone screw shank.

In some embodiments, the bone screw 6 is a polyaxial bone screw 6*a*, such as is shown in FIGS. 5-17. In other embodiments, the bone screw 6 is a monoaxial bone screw 6*b*, such as is shown in FIGS. 18-25, and which includes a fixed, non-movable head 12. In the case of polyaxial bone screws 6*a*, the shank 10 includes an upper portion 10*a* with a drive feature 10*b* that extends into the head 12 and is operationally secured therein, so that the head 12 is rotatable on the shank 10 until locked in position through engagement with the rod 4 under pressure. As shown in the illustrated embodiment shown in FIG. 10, the drive feature 10*b* is a hex-shaped upward projection adapted for engaging a driver with a complementary socket head, such as is known in the art. Additional or alternative drive features are foreseen. In particular, when the rod 4 is placed within an associated U-shaped channel 16, the rod 4 contacts or engages the drive feature 10*b* (see FIG. 15) and thereby urges the upper portion 10*a* downwardly whereby the upper portion 10*a* frictionally locks the shank 10 in position in a fixed angular position relative to the head 12. For example, FIG. 12 illustrates using the guide tool 1 to position the bone screw head 12 at an angle with respect to the shank 10. In some embodiments, the polyaxial bone screw 6*a* includes a pressure insert (not shown) that transfers a downward forced from the rod 4 to the bone screw upper portion 10*a*, so as to lock the position of the head 12 relative to the shank 10. It is foreseen that the bone screw 6 may include an upper pressure insert (not shown). Many different conventional bone screws where the head locks relative to the shank are well known in the art. It is noted that the monoaxial bone screw 6*b* also includes a drive feature 10*b* such as but not limited to a slot-shaped region sized and shaped to releasably engage a flat-head driver (not shown), such as is known in the art.

The present invention is not intended to be restricted to a particular type of bone screw. In the present embodiment, a polyaxial type bone screw 6*a* is utilized wherein the shank 10 is locked in position by direct or indirect contact with the rod 4. It is foreseen that a tool set including the guide tool 1 of the present invention can be used with virtually any type of bone screw, including polyaxial bone screws 6*a* of many different types wherein the head 12 is locked relative to the shank 10 by structure other than in the manner described in the illustrated embodiment, and also including monoaxial bone screws 6*b* and hooks.

Figure 5:
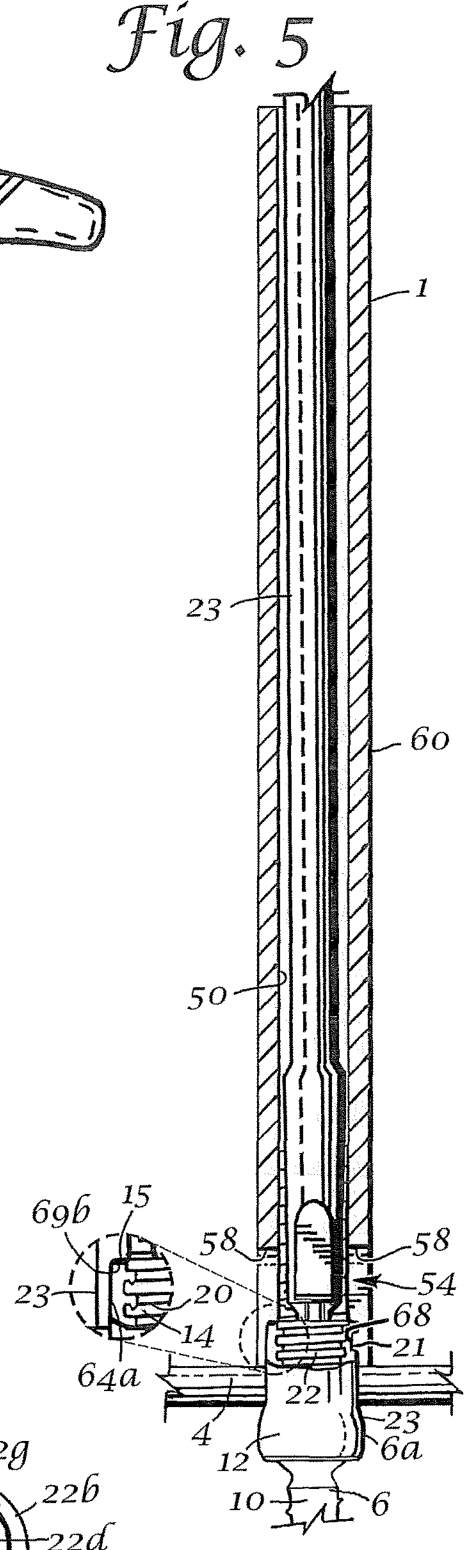
FIG. 5 is an enlarged view of a portion of the tool of FIG. 4 including a polyaxial bone screw adapted for use with the tool of FIG. 1, a rod, the closure of FIG. 4 and the closure driver of FIG. 4, showing attachment of the guide tool to the bone screw and installation of the closure top into the bone screw head using the closure driving tool, so as to secure a rod in the bone screw head.
Figure 6:
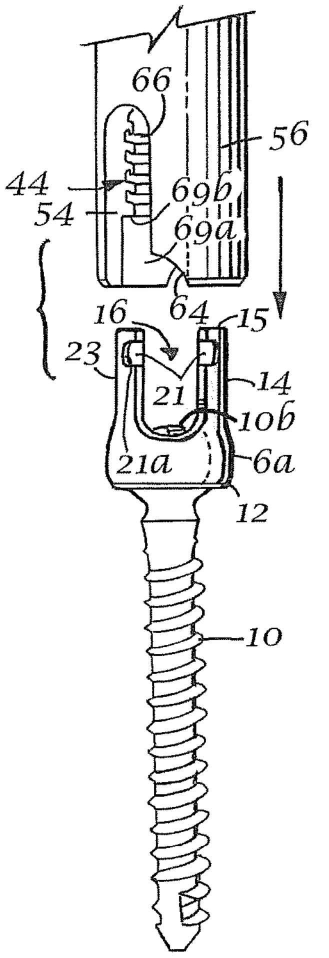
FIG. 6 an enlarged side view of the guide tool of FIG. 1 with portions broken away showing an initial step in reversibly attaching the guide tool to the polyaxial bone screw of FIG. 5.
Figure 18:
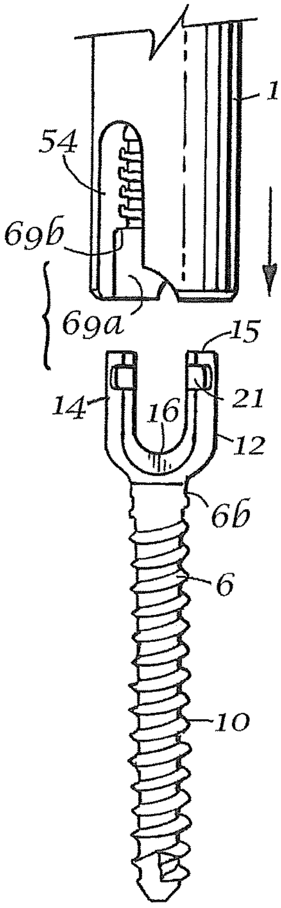
FIG. 18 is an enlarged side view of the guide tool of FIG. 1, with portions broken away, illustrating an initial step in reversibly attaching the guide tool of FIG. 1 to a monoaxial bone screw adapted for use with the guide tool.
Figure 19:
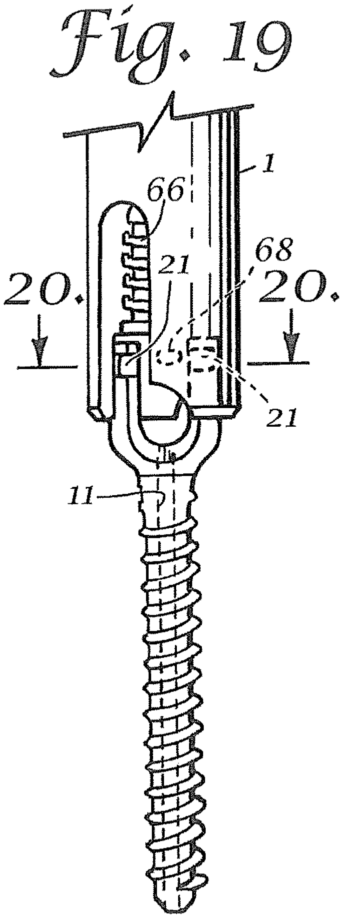
FIG. 19 is a side view of the guide tool of FIG. 18 illustrating an intermediate step in attaching the guide tool to the monoaxial bone screw, wherein the guide tool through-slot is not yet aligned with the bone screw U-shaped channel.
Figure 21:
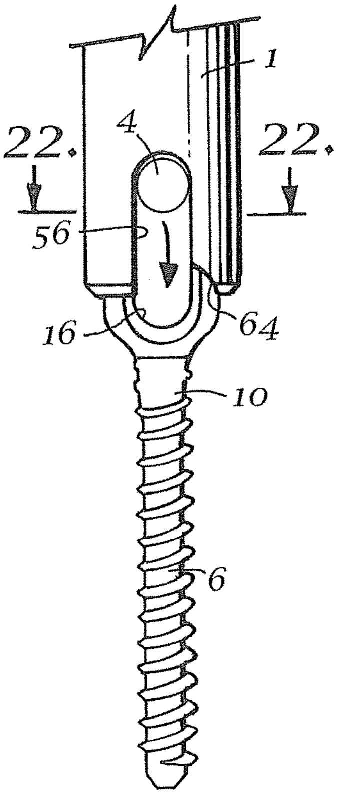
FIG. 21 is a side view of the guide tool of FIG. 19 showing the guide tool reversibly attached to the monoaxial bone screw of FIG. 18, wherein the guide tool through-slot is substantially aligned with the bone screw U-shaped channel.
Figure 21A:
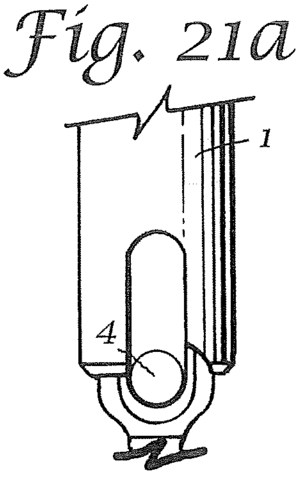
FIG. 21*a* is a side view of the assembly of FIG. 21, with portions broken away, showing the rod reduced into the bone screw U-shaped channel.
Figure 20:
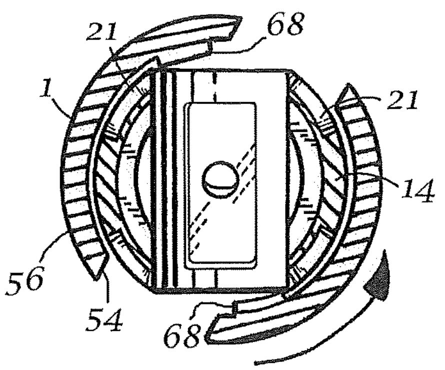
FIG. 20 is an enlarged cross-section of FIG. 19 taken along the line 20-20 of FIG. 19 and illustrating the an initial step in aligning and engaging the guide tool bone screw attachment structure with the complementary bone screw tool engagement structure.
Figure 22:
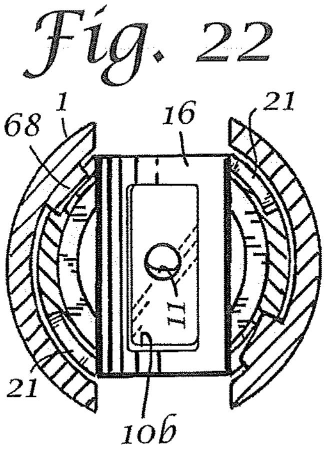
FIG. 22 is an enlarged cross-section of FIG. 21 taken along the line 22-22 of FIG. 21 showing the guide tool bone screw attachment structure reversibly engaged with the bone screw tool engagement structure.
Figure 23:
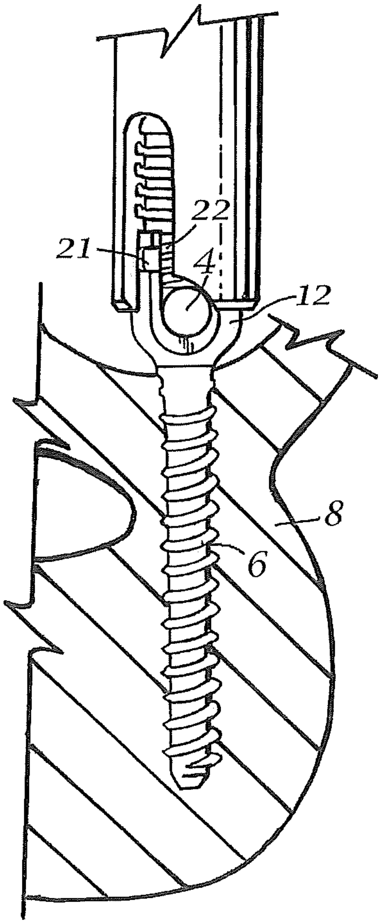
FIG. 23 is a side view of the guide tool and monoaxial bone screw of FIG. 21 illustrating a step in detaching the guide tool from the monoaxial bone screw after installation of a rod and a closure top into the monoaxial bone screw.

Referring to FIGS. 6 and 18, each bone screw head 12 has a pair of upstanding arms 14. The upstanding arms each include an upper surface 15 and define a U-shaped rod-receiving channel, generally 16. The arms 14 include inner surfaces 18 with an internal guide and advancement structure, feature, portion or member 20 (see FIG. 5) thereon. The arms 14 each include an off-axis or circumferentially located tool engagement structure 21, also referred to as an engagement structure, portion or member, such as but not limited to a slot-like structure, channel or bore, that extends at least partially circumferentially about the periphery of the arms 14. While the tool engagement structure 21 of the illustrated embodiment is located on the arms 14, an attachment structure for this purpose could be located anywhere on the bone screw head 12. The bone screw's tool engagement structure 21 is sized, shaped and positioned so as to reversibly receive, engage or mate with a complementary engagement structure of the guide tool 1, which is described below.

A closure top 22 adapted for use with the bone screw 6 is received in the U-shaped channel 16, so as to lock the rod 4 therein. When the bone screw is a polyaxial bone screw 6*a*, locking the closure top 22 in the U-shaped channel 16 also locks the head 12 in place at a selected angle relative to the shank 10, such that the head 12 is substantially stationary or immobilized.

Figure 4:
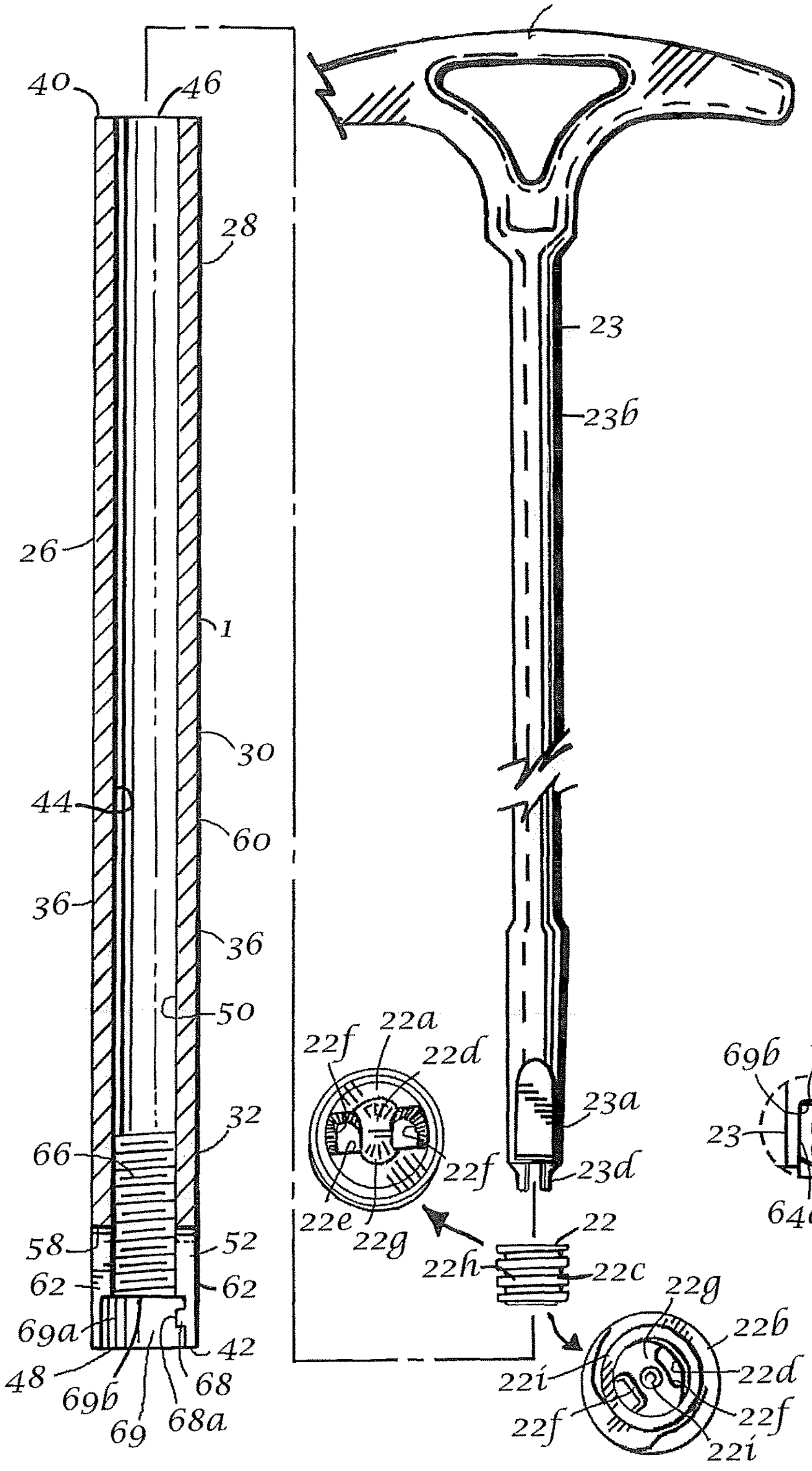
FIG. 4 is a cross section of the tool of FIG. 2 taken along line 4-4 of FIG. 2, including a closure top adapted for use with the guide tool and a closure installation tool or driver for installing the closure top into a bone screw attached to the guide tool, and including enlarged top and bottom views of the closure.

Referring to FIGS. 4, 5, 34 and 35, the closure top 22 includes top, bottom and side surfaces 22*a*, 22*b*, 22*c*, respectively, and at least one drive feature or imprint 22*d*. In the illustrated embodiment, the drive feature 22*d* includes a recessed slot member 22*e* and a pair of spaced pin engagement bores 22*f*. The pin engagement bores are separated by a bridge portion 22*g* and join the top and bottom surfaces 22*a* and 22*b*. Accordingly, the closure drive feature 22*d* is engaged by the driver 23, such as is shown in FIGS. 4 and 5, or alternatively by a flat-head screw driver. Alternative drive features 22*d* are foreseen, such as but not limited to a hex-shaped break-off head (see FIG. 34). The closure side surface 22*c* includes a guide and advancement structure 22*h* that is complementary to the bone screw guide and advancement structure 20. The bottom surface 22*b* includes a rod engagement feature 22*i*, which may include one or more of a downwardly extending ring, ridge, point, detent, or knurl. The rod engagement feature 22*i* is adapted to bite, cut into or compress the rod 4 when the closure 22 is secured or locked in the U-shaped channel 16, thereby securing the rod 4 therein. Alternative rod engagement features 22*i* are foreseen.

Figure 34:
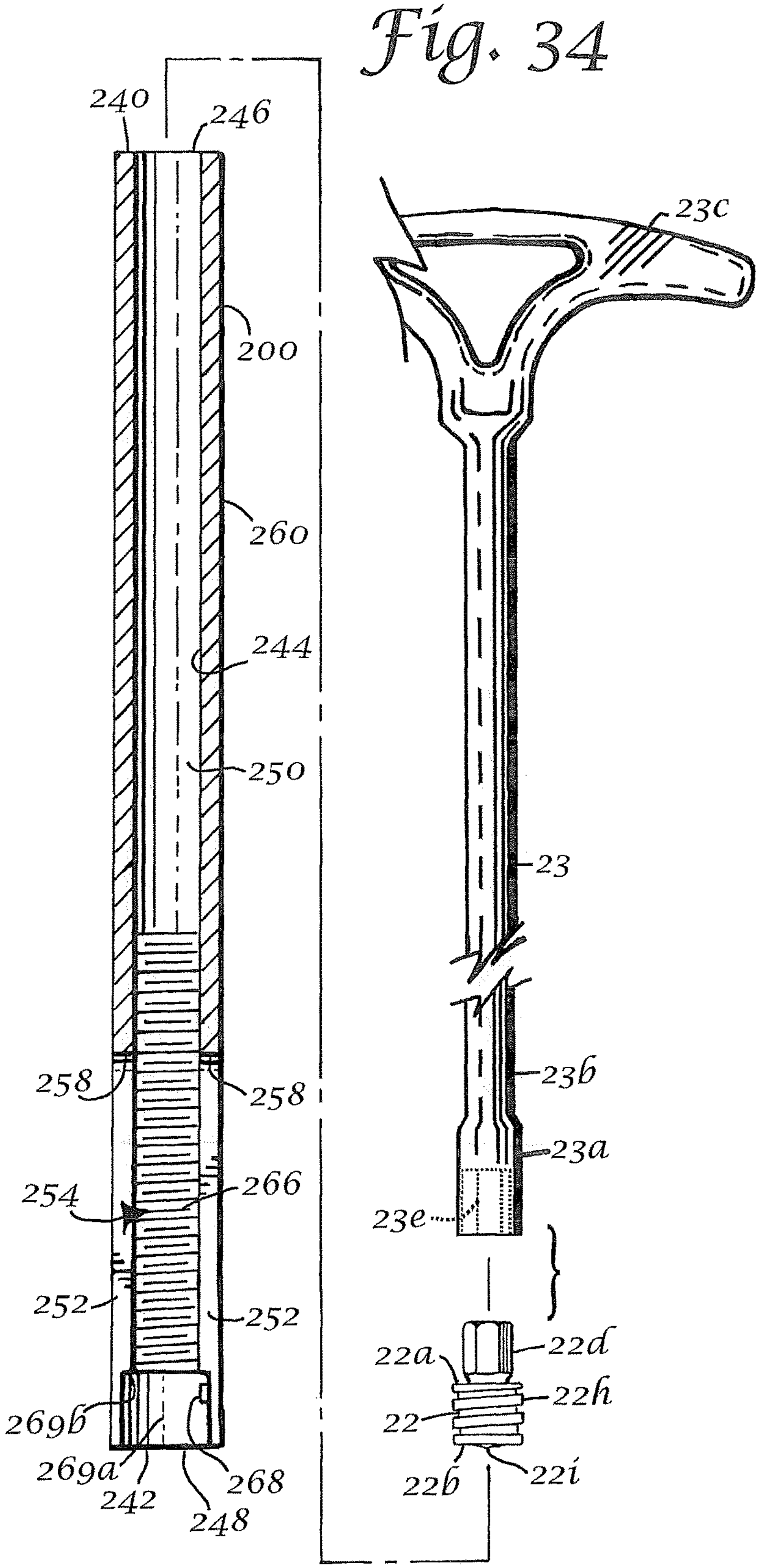
FIG. 34 is a cross-section of the guide tool of FIG. 26 taken along the line 34-34 of FIG. 27, and illustrating a closure top, with a break-off head, adapted for use with the guide tool and a closure driver adapted for use with the closure top, wherein certain portions of the closure driver are shown in phantom to show greater detail thereof.
Figure 35:
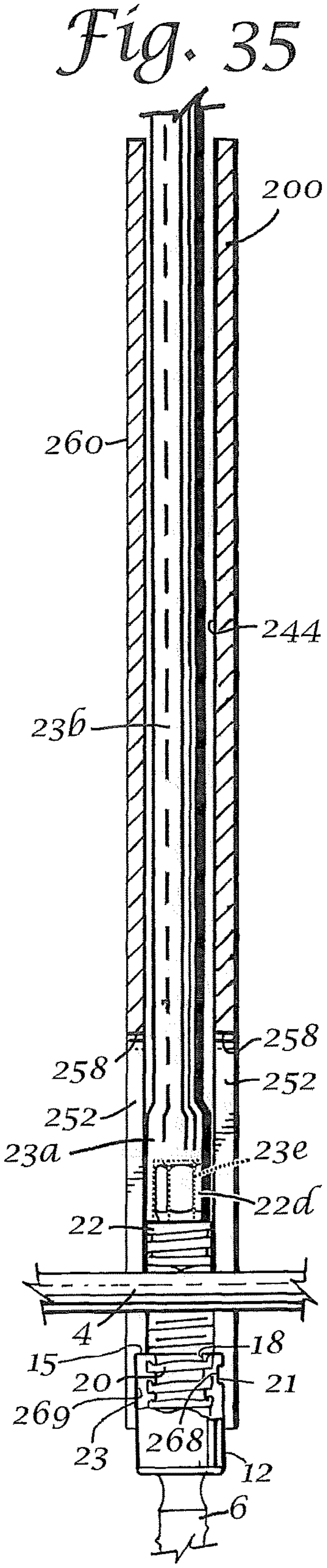
FIG. 35 is a view of the components of FIG. 34, with portions broken away, illustrating a step of installing a rod into the polyaxial bone screw of FIG. 29 in conjunction with installing the closure top of FIG. 34 using the closure driving tool of FIG. 34.
Figure 36:
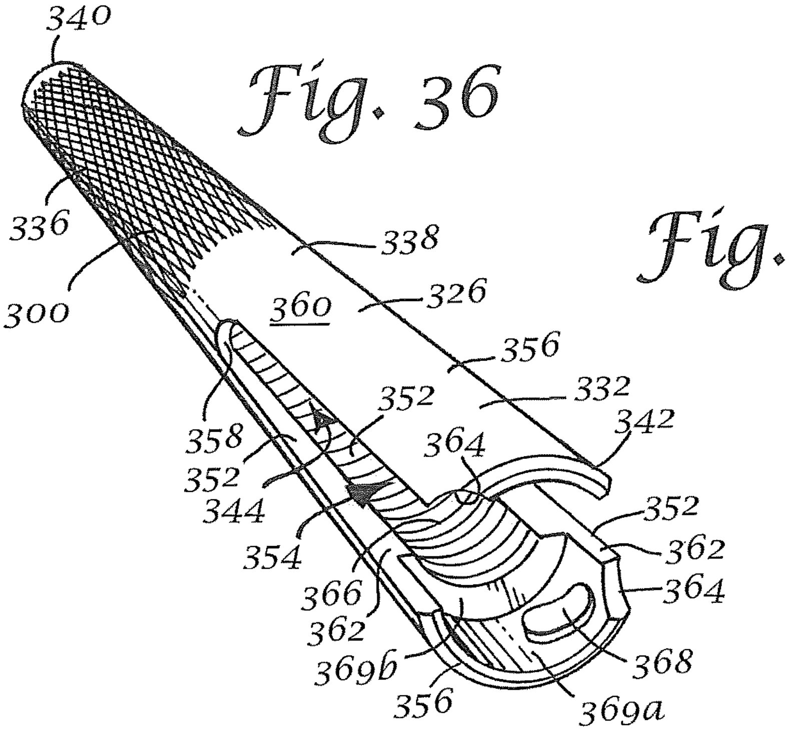
FIG. 36 is perspective view of a guide tool for percutaneously implanting a rod in a patient, in a third embodiment.
Figure 37:
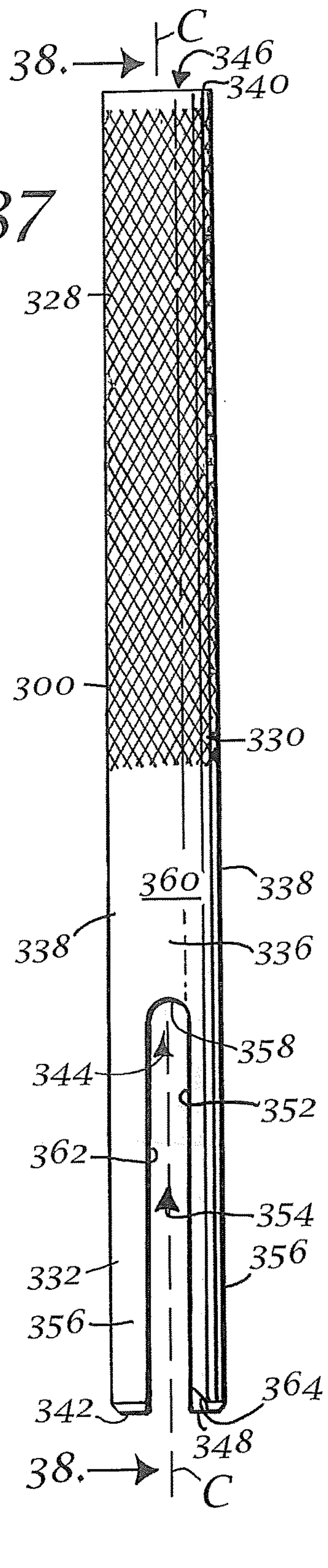
FIG. 37 is a reduced side view of the guide tool of FIG. 36.
Figure 38:
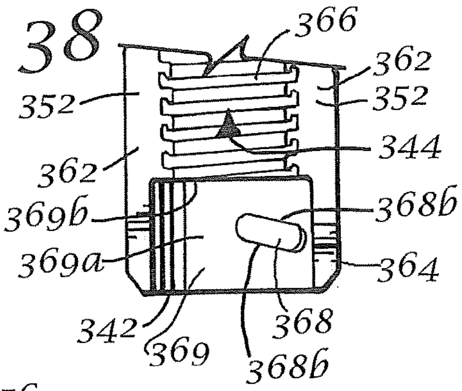
FIG. 38 is an enlarged cross-sectional view of the guide tool of FIG. 36 taken along line 38-38 of FIG. 37, with portions broken away.
Figure 39:
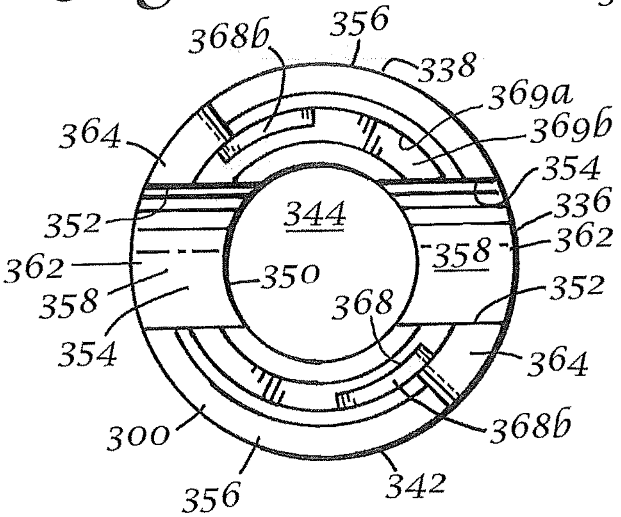
FIG. 39 is an enlarged bottom view of the guide tool of FIG. 36.
Figure 40:
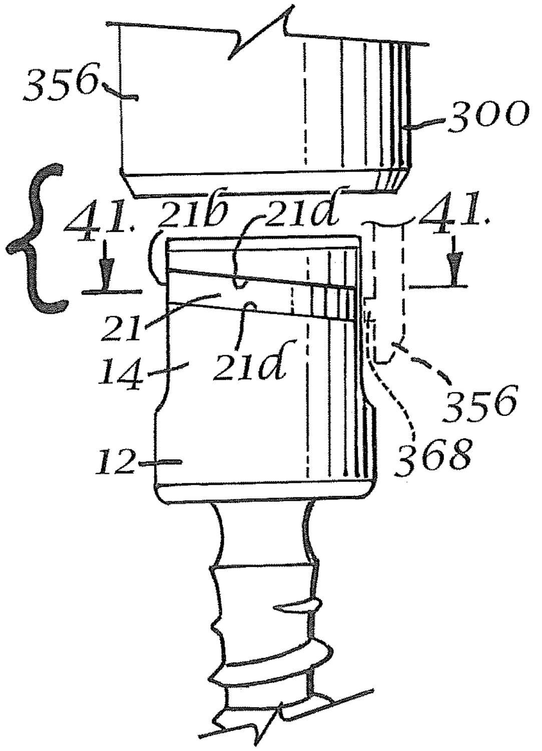
FIG. 40 is an enlarged side view of the guide tool of FIG. 36, with portions broken away to illustrate an initial step in attaching the guide tool of FIG. 36 to a polyaxial bone screw adapted for use with the guide tool, and also showing a portion of the guide tool in phantom to illustrate alignment of the guide tool bone screw attachment structure with the bone screw tool engagement structure.
Figure 42:
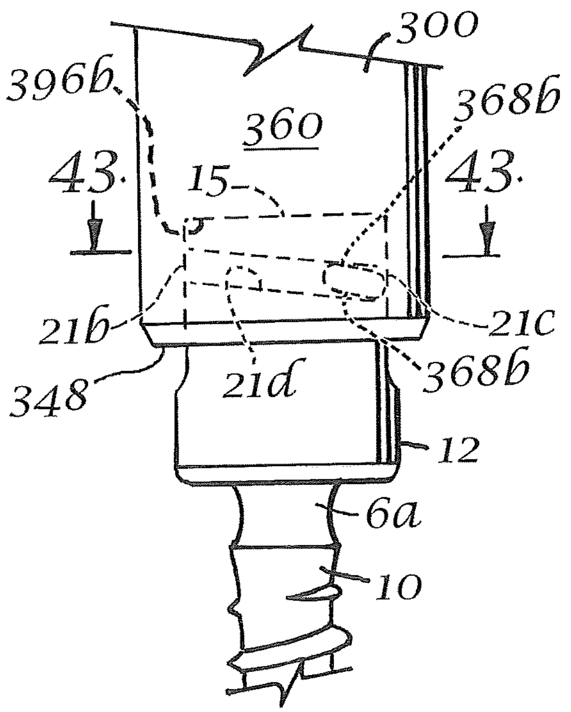
FIG. 42 is side view of the guide tool of FIG. 40, with portions broken away, showing the guide tool reversibly attached to the polyaxial bone screw.
Figure 41:
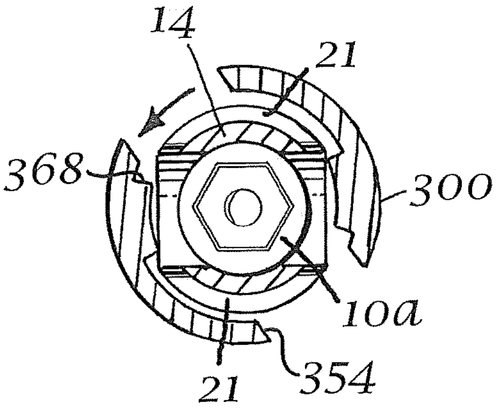
FIG. 41 is a cross-section of the guide tool and bone screw of FIG. 40 taken along line the 41-41 of FIG. 40 illustrating an initial step in aligning and engaging the guide tool bone screw attachment structure with the complementary bone screw tool engagement structure.
Figure 43:
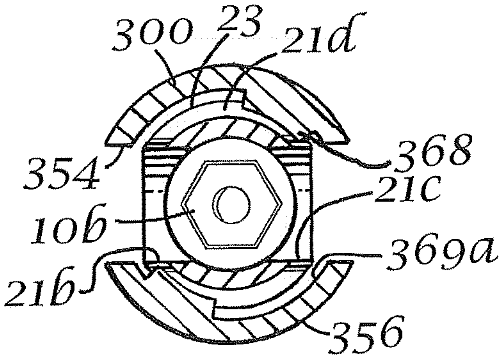
FIG. 43 is a cross-section of the guide tool and bone screw of FIG. 42 taken along line the 43-43 of FIG. 42 showing the guide tool bone screw attachment structure reversibly engaged with the bone screw tool engagement structure.
Figure 44:
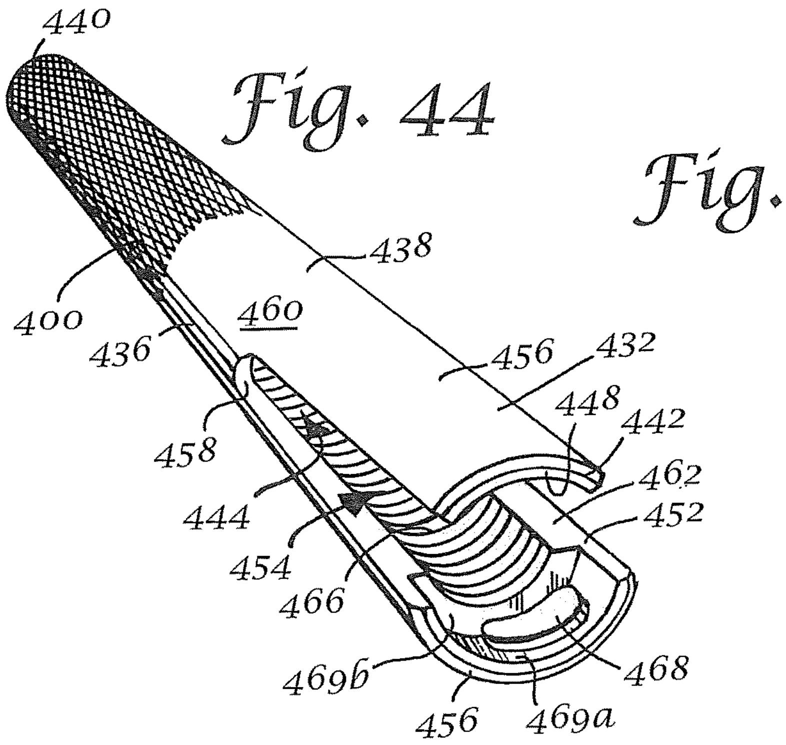
FIG. 44 is perspective view of a guide tool for percutaneously implanting a rod in a patient, in a fourth embodiment.
Figure 45:
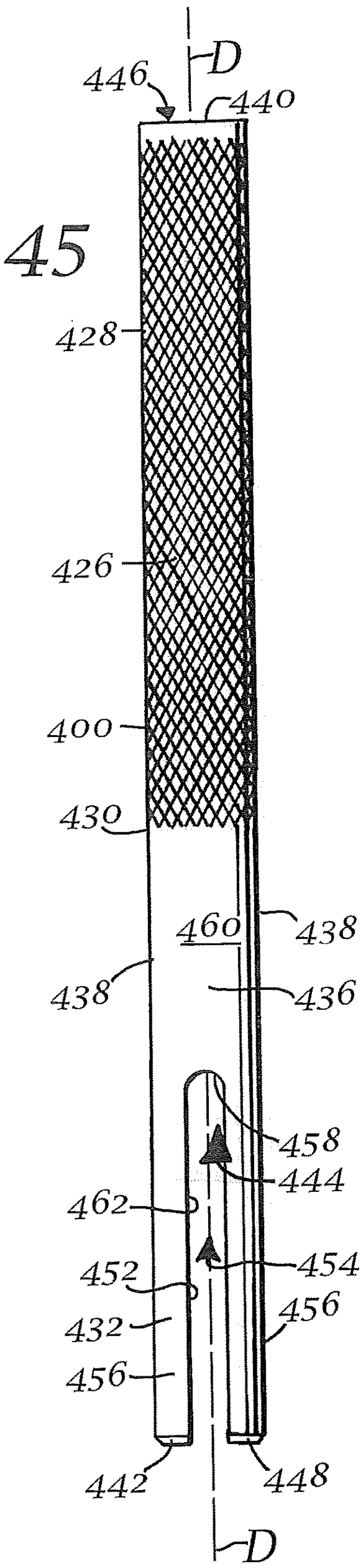
FIG. 45 a reduced side view of the guide tool of FIG. 44.
Figure 46:
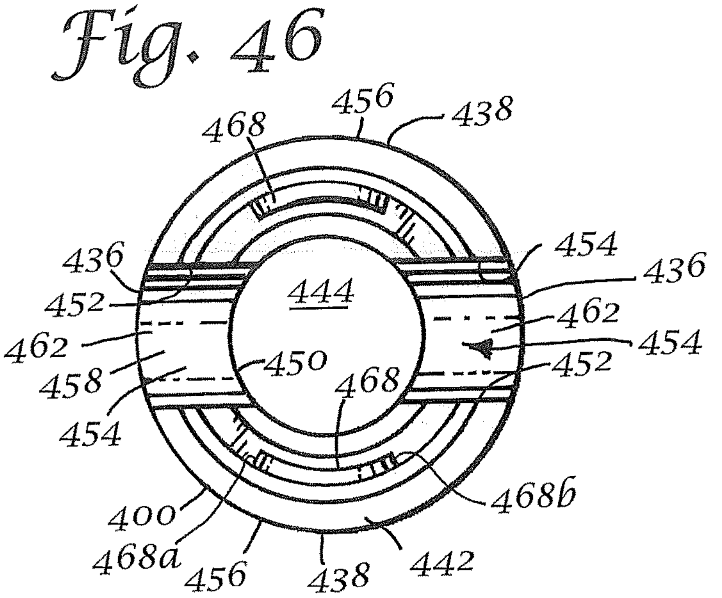
FIG. 46 is an enlarged bottom view of the guide tool of FIG. 44.

Still referring to FIGS. 4, 5, 34 and 35, the closure drive feature 22*d* is reversibly engaged by a closure driver 23 that is sized and shaped to be received through the guide tool 1, such as is shown in FIGS. 5 and 35 and described below. The closure driver 23 includes a head member or portion 23*a*, or imprint engagement structure, that is complementary to the closure drive feature 22*d*. The closure driver 23 also includes a shaft 23*b* and a handle 23*c*. In an exemplary embodiment shown in FIGS. 4 and 5, the driver head 23*a* include a pair of spaced downwardly extending pin members 23*d*, or fingers, that are spaced apart a distance substantially equal to the width of the closure bridge portion 22*g* and are also sized and shape to be reversibly received into and optionally through the pin engagement bores 22*f*, such that the closure driver 23 can rotate or screw the closure 22 into the bone screw 6. In another exemplary embodiment shown in FIGS. 34 and 35, the head 23*a* includes a hex-shaped socket 23*e* that is adapted to reversibly engage a complementary mating hex-shaped break-off closure head or drive feature 22*d*. It is foreseen that other closures may be used in conjunction with the bone screw 6. Accordingly, a closure driver 23 for use with such a closure 22 includes a head 23*a* adapted to engage the drive feature or imprint 22*d* of the closure 22.

The bone screw head 12 also includes an exterior surface 24. Additional details of bone screws for use with the present invention can be found in U.S. Pat. No. 7,776,067, which is incorporated by reference herein.

Referring again to FIGS. 1-25, in a first embodiment the guide tool 1 of the present invention has a substantially cylindrical elongate body 26 that is sized and shaped to be sufficiently long to extend from an attached implanted bone screw 6 through an exterior of a patient's skin so as to provide an outwardly extending upper handle portion 28 that allows and provides for gripping by a surgeon during procedures utilizing the guide tool 1. In addition to the handle portion 28, the guide tool body 26 includes an intermediate or middle portion 30 and a lower portion 32 along the length thereof.

The body 20 includes front and rear walls 36 and side walls 38, wherein the walls 36 and 38 extend from a top or top end 40 to a bottom or bottom end 42 of the guide tool 1. A cylindrical through-bore, generally 44, or through-channel, extends axially through the guide tool body 26 so as to join a first or top opening, generally 46, located at the top end 40 with a second or bottom opening 48 located at the bottom end 42. The longitudinally extending through-bore 44 is coaxial with the guide tool longitudinal axis A, has a substantially smooth cylindrical inner surface 50 and is sized and shaped to receive therethrough at least the closure top 22 for closing the bone screw 6. Accordingly, the closure top 22 is adapted or sized and shaped for use with the guide tool 1. The through-bore 44 is also sized so as to receive there through a closure driver 23 (see FIGS. 4-5, 11 and 13-15), and optionally additional tools, such as but not limited to a bone screw driver 51 (see FIG. 11) and a guide wire 11*a*. It is noted that the bone screw driver 51 includes a head portion 51*a* adapted to engage the bone screw shank drive feature 10*b*, a shaft 51*b*, a handle 51*c* and optionally a longitudinally extending cannula 51*d* that extends longitudinally or axially upwardly from the head 51*a*, so as to join a cannula opening located in the driver's head portion 51*a* with an opening 51*e* located at the top of the handle portion 51*c*. The driver's cannula 51*d* receives the guide wire 11*a* and aids in positioning the bone screw 6. For example, when implanting the bone screw 6, the guide wire 11*a* is generally implanted in the vertebra 8. Then the guide tool 1 and the bone screw 6 are engaged with one another, and the bone screw 6 is placed over the guide wire 11*a*, such as through the cannula 11 in the bone screw shank 10, until the tip 10 of the shank contacts the vertebra 8. The driver 51 is then inserted through the guide tool 1 such that the head 51*a* engages the shank's drive feature 10*b* and the guide wire 11*a* is received through the driver's cannula 51*d*, such as is shown in FIG. 11. The driver 51 is then used to drive the shank 10 into the bone 8 by applying torque to the shank 10, such as is known in the art. After the bone screw 6 has been implanted into the vertebra 8, the driver 51 is removed from the guide tool 1, and the rod implantation procedure is continued, such as is known in the art.

The guide tool 1 includes a cutout portion, region or surface 52 that is located at or near the bottom 42, wherein a portion of each of the front and rear walls 36 of the through-bore 44 are removed in order to provide a slot-shaped region, generally 54, also referred to as a through-slot, rod-receiving member, portion or channel 54. The cutout portions 52 are parallel and opposed to one another and extend from the bottom longitudinally toward the intermediate portion 30 of the guide tool body 26. The through-slot 54 is substantially alignable with the bone screw U-shaped channel 16, and is also sized and shaped to allow passage of the rod 4 therethrough (see FIGS. 9-11, 13-15 and 21-22), such as is described below. The through-slot 54 extends through the front and rear walls 36 of the body 26, such that the side walls 38 form downwardly extending, spaced opposed legs, members or tangs 56. Thus, the body lower portion 26 includes the through-slot 54 and the legs 56. The cutout portion 52 includes an upper slot surface 58 that may be arch-shaped, U-shaped, planar or the like. In some embodiments, portions the body outer surface 60 adjacent to the through-slot openings 62 are beveled, slanted or partially conical, so as to guide, direct or assist in threading or passing an end of the rod 4 into the opening 62 of the through-slot 54.

At or near the bottom 38 of the body 26, the guide tool 1 includes a rod abutment recess or relief 64. The relief 64 is sized and shaped for the purpose of bridging the rod 4 when the guide tool 1 is rotated for removal, such as to twist the guide tool 1 off of the bone screw head 12, as described elsewhere herein (see FIGS. 16 and 23).

Figure 9:
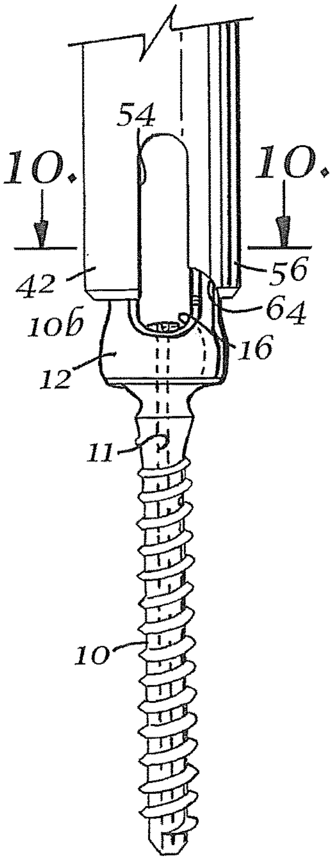
FIG. 9 is a side view of the guide tool of FIG. 7 showing the guide tool of FIG. 1 reversibly attached to a polyaxial bone screw of FIG. 6, wherein the guide tool has been rotated about 90-degrees clockwise relative to the bone screw head and the guide tool through-slot is substantially aligned with the bone screw U-shaped channel.
Figure 10:
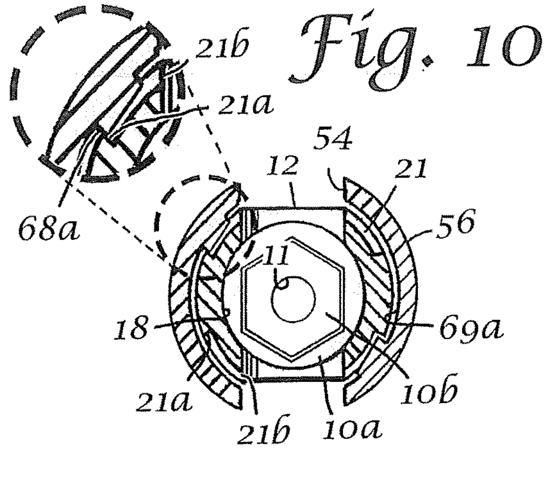
FIG. 10 is an enlarged cross-sectional view of the guide tool and bone screw of FIG. 9 taken along the lines 10-10 of FIG. 9 and illustrating reversible engagement of the guide tool bone screw attachment structure with the bone screw tool engagement structure.

Also near the bottom 38 of the body 26, the guide tool's through-bore 44 includes a helically wound or partially helically wound guide and advancement structure 66 which may include conventional helical threads, helically wound square threads, a flange form, or other guide and advancement structure sized and shaped to cooperate with complementary equivalent or mateable structure within the bone screw head 12, such as for example the guide and advancement structure 20 on the bone screw arms 14 and the guide and advancement structure 22*h* located on the side 22*c* of the closure top 22. The tool guide and advancement structure 66 is located or adapted such that when the guide tool 1 is mounted on, engaged with or attached to the bone screw 6, such as when the through-slot 54 is substantially aligned with the U-shaped channel 16, such as is shown in FIGS. 9 and 10 for example, the closure 22 is smoothly and rotatably transferable from the guide tool through-bore 44 to the bone screw U-shaped channel 16.

The guide tool 1, of the first embodiment, includes at least one radially inward facing bone screw attachment structure 68, also referred to as a bone screw engagement structure or first attachment structure, that is located at or near the bottom opening 48. For example, as shown in FIGS. 1-4, 8 and 10, in the illustrated embodiment, the inner surface 50 of each leg 56 includes a bone screw attachment structure 68. Generally, the tool's bone screw attachment structure 68 includes at least one of a radially inwardly extending projection, flange, shoulder, shelf, arm, detent, hook member or the like on at least one of the leg the inner surfaces 50. As described in greater detail below, the tool's bone screw attachment structure 68 is sized, shaped and adapted to releasably and cooperatively engage or mate with a complementary attachment structure of the bone screw 6, whereby the guide tool 1 and the bone screw 6 are releasably locked together, which in turn facilitates alignment of the guide tool's through-slot 54 with the bone screw's U-shaped channel 16. It is noted that numerous complementary and cooperative sized, shaped and configurations of the guide too's bone screw attachment structure 68 and the bone screw's tool engagement structure 21 are foreseen. Additionally, at least a portion of these structures 68 and 21 may be located elsewhere on the respective structure 1 or 6.

To facilitate engagement between the bone screw's tool engagement structure 21 and guide tool's screw attachment structure 68, the guide tool 1 also includes a mating chamber, cup, portion or area 69. This mating chamber 69 is sized and shaped to receive therein at least an upper portion of the bone screw head 12, such as but not limited to the bone screw's arms 14, and further to reversibly engage the tool engagement structure 21 located on the exterior surface 23 of the bone screw arms 14. In the exemplary embodiment shown in FIG. 1, the mating portion 69 includes a discontinuous cylindrical inner chamber 69*a*, a pair of crescent-shaped planar screw abutment surface 69*b*, and the radially inwardly facing attachment structure 68. Alternatively shaped mating portions 169 are foreseen.

Figure 7:
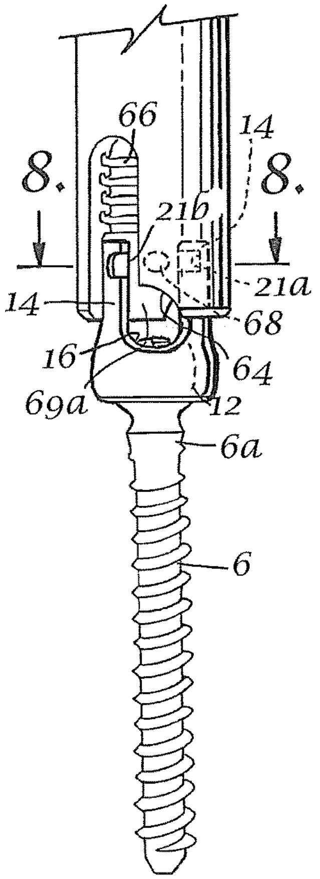
FIG. 7 is a side view of the guide tool of FIG. 6 showing an intermediate step in attaching the guide tool of FIG. 1 to the polyaxial bone screw of FIG. 6, wherein the through-slot of the guide tool is not yet aligned with the U-shaped channel of the bone screw.
Figure 8:
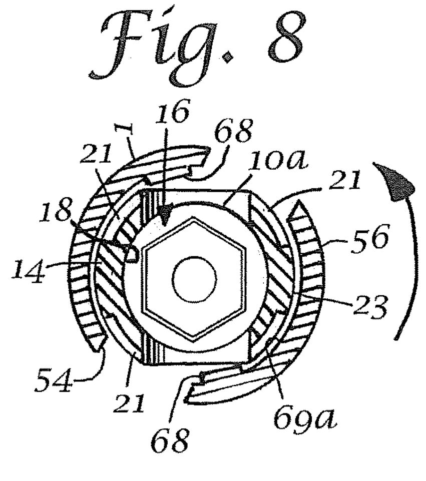
FIG. 8 is an enlarged cross-sectional view of the guide tool and bone screw of FIG. 7 taken along the line 8-8 of FIG. 7 and illustrating the an initial step in aligning and engaging the guide tool bone screw attachment structure with the complementary bone screw tool engagement structure.

Referring to FIGS. 6-8, when the guide tool 1 is mounted on a bone screw head 12, the mating portion 69 extends downwardly around a portion of the head 12, or receives the bone screw arms 14 therein, such that the mating portion's screw abutment surfaces 69*b* contact or abut the arm top surfaces 15. Additionally, the inner chamber surface 69*c* contacts the bone screw arm 14 exterior surfaces 23. Initially, as shown in FIGS. 7 and 8, the guide tool's bone screw attachment structure 68 is vertically aligned with but not engaged with the bone screw's tool engagement structure 21. When in this configuration, the guide tool's through-slot 54 is not aligned with the bone screw's U-shaped channel 16. As shown in FIGS. 9 and 10, the attachment structure 68 and the engagement structure 21 are cooperatively mated together by rotating the guide tool 1 counter-clockwise relative to the bone screw head 12. In the illustrated embodiment, the amount of rotation is about 90-degrees. This rotation slides the tool's screw attachment structure 68 into the bone screw's tool engagement structure 21, whereby the structures 68 and 21 are reversibly and cooperatively interlocked or mated, such that the guide tool 1 and the bone screw 6 are reversibly locked together. When engaged in this manner, the guide tool 1 may be said to be mounted on the bone screw 6.

It is noted that the bone screw's tool engagement structure 21 includes a stop or abutment surface 21*a*. The tool's screw attachment structure 68 includes another stop or abutment surface 68*a*, also referred to as a leading surface, that is adapted to cooperatively engage the stop 21*a*. When the guide tool's screw attachment structure 68 is mated with the bone screw's tool engagement structure 21, the respective abutment surfaces 68*a* and 21*a* cooperatively abut or engage one another, thereby preventing further rotation of the guide tool 1 with respect to the bone screw head 12. Accordingly, this abutment of the surfaces 68*a* and 21*a* ensures that the guide tool 1 is not over-rotated, so that the tool's through-slot 54 and the bone screw's U-shaped channel 16 are substantially aligned, such as is shown in FIGS. 9-10. It is foreseen that the attachment and engagement structures 68 and 21, respectively can be sized and shaped such that the amount of rotation required to alight the through-slot 54 with the U-shaped channel 16 may be somewhat larger or smaller the 90-degrees. When the through-slot 54 and the U-shaped channel 16 are substantially aligned, a rod 4 and a closure 22 can be moved, passed, transferred or slid from the guide tool 1 to the attached bone screw 6.

Alternative structures and methods for engaging or mounting the guide tool 1 and the bone screw 6 together are foreseen. For example, in some embodiments, the bone screw's tool engagement structure 21 includes additional locking structure that enables locking the guide tool 1 with the bone screw 6 by pulling the guide tool 1 slightly axially upward relative to the respective bone screw 6.

Figure 15:
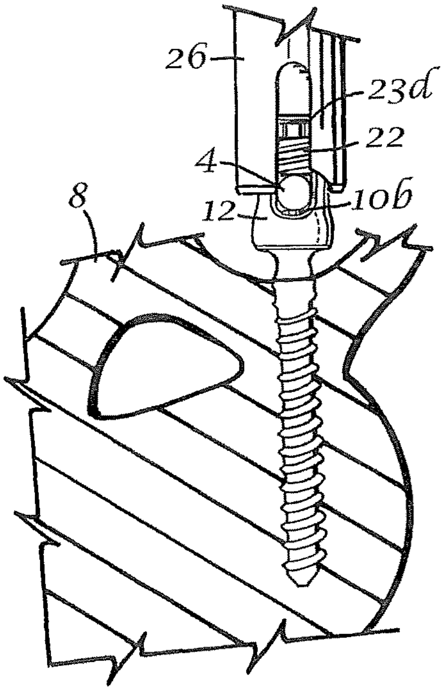
FIG. 15 is a side view of the guide tool of FIG. 14 in a further step of installing the rod and the closure top into the bone screw U-shaped channel using the closure installation tool.
Figure 16:
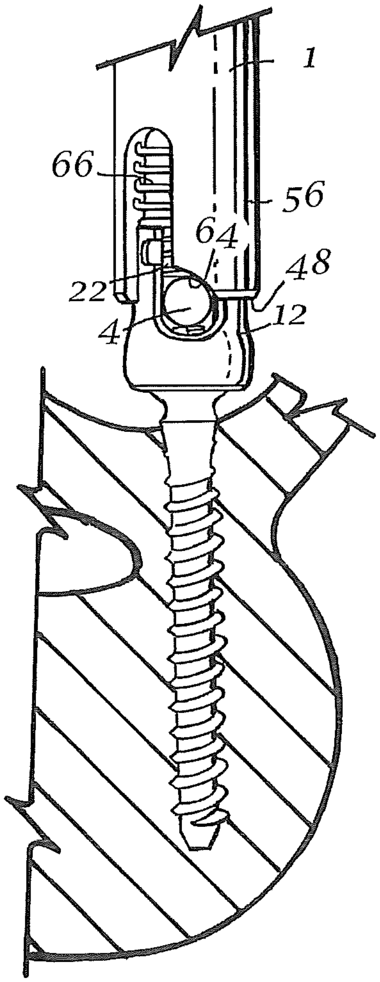
FIG. 16 is a side view of the guide tool of FIG. 15 illustrating an initial step in disengaging the guide tool from the bone screw after installation of the rod and the closure top in the bone screw.
Figure 17:
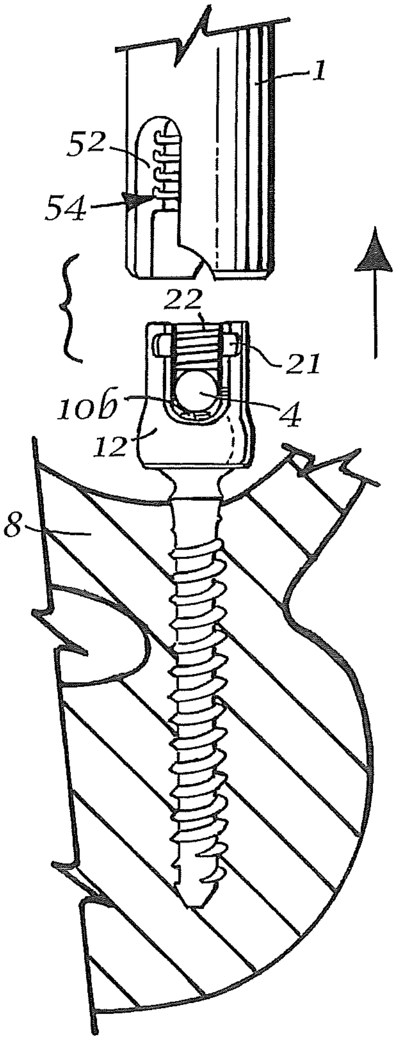
FIG. 17 is a side view of the guide tool of FIG. 16, illustrating a further step in the removal of the guide tool removed from the bone screw.

The guide tool 1 is disengaged from the bone screw 6 using a twist-off maneuver, wherein the guide tool 1 is rotated 90-degrees clockwise from an attaching configuration, such as is described above, when viewing from the top so as to disengage the guide tool's screw attachment structure 68 from the bone screw's tool engagement structure 21 (e.g., see FIGS. 15-17). In some instances, the guide tool 1 is rotated somewhat more or less than 90-degrees to make the necessary alignment for removal, which depends on the specific construction of the parts.

In this manner, the guide tools 1 twists off of respective bone screws 6 and in the particular illustrated embodiment the guide tools 1 are also assembled on the bone screws 6 by the opposite twist-on maneuver, which is the reverse of the twist-off maneuver. In certain embodiments where there is enough flexibility in the legs 56, such that the legs 56 can be splayed radially outwardly at the bottom 42 thereof, so the guide tool 1 snaps-on over the bone screw 6.

Referring now to FIGS. 16 and 17, the space 54 between the guide tool legs 56 that is equivalent to the width of the through-slot's opening 62 is preferably substantially equivalent to the space between the bone screw's arms 14 so that the through-bore 44, or the slot-shaped region 54, aligns with the U-shaped channel 16 when the guide tool 1 is mounted on a respective bone screw 6. The guide tool's rod-abutment recess 64 is sized, shaped and positioned such that when the rod 4 is located, fixed, implanted or installed in the bone screw 6, the guide tool 1 can rotate about the tool's longitudinal axis A and the rod-abutment recess 64 allows the guide tool 1 to straddle over the rod 4, thereby allowing the guide tool 1 to twist relative to the bone screw 6 and free the guide tool's bone screw attachment structure 68 from the bone screw's tool engagement structure 21 and thereafter be removed after all procedures are complete, as described below. Without such a rod-abutment recess 64, when the guide tool 1 was rotated clockwise for disconnection from the bone screw 6, movement of the legs 56 would be blocked or hindered by the rod 4. As a result, the guide tool 1 would likely have to be pried off of the bone screw 6, so as to be removed therefrom.

Closure top 22, also referred to as an enclosure, closes between the spaced bone screw arms 14 so as to secure the rod 4 in the channel 16. The closure top 22 can be any of many different plug type closures known in the art. Preferably the closure top 22 has a cylindrical body that has a helically wound mating closure guide and advancement structure 22*h*. The closure's guide and advance at structure 22*h* can be of any type, including V-type threads, buttress threads, reverse angle threads, or square threads. Preferably the closure's guide and advancement structure 22*h* is a helically wound flange form that interlocks with a reciprocal flange form as part of the guide and advancement structure 20 on the interior of the bone screw arms 14. A suitable locking guide and advancement structure of this type is disclosed in U.S. Pat. No. 6,726,689, which is incorporated herein by reference. Referring to FIGS. 4-5, the guide tool's helical wound guide and advancement structure 66, which is located in the lower portion 32 of each of the guide tools 1, is sized and shaped to receive the mating guide and advancement structure 22*h* of the closure top 22. When the U-shaped channel 16 and the through-slot 54 are aligned, the bone screw's guide and advancement structure 20 forms a generally continuous helically wound pathway with the tool's guide and advancement structure 66, but does not require locking between the closure top 22 and the tool 1, even when a locking flange form is utilized on the closure top 22. Further, when the U-shaped channel 16 and the through-slot 54 are aligned, can be rotatably passed between the guide tool 1 and the bone screw 6, such as is shown in FIG. 5. This enables the rod 4 to be reduced into and seated in the U-shaped channel 16 using the closure top 22 and the associated closure driver 23, such as is shown for example in FIGS. 13-15.

Figure 13:
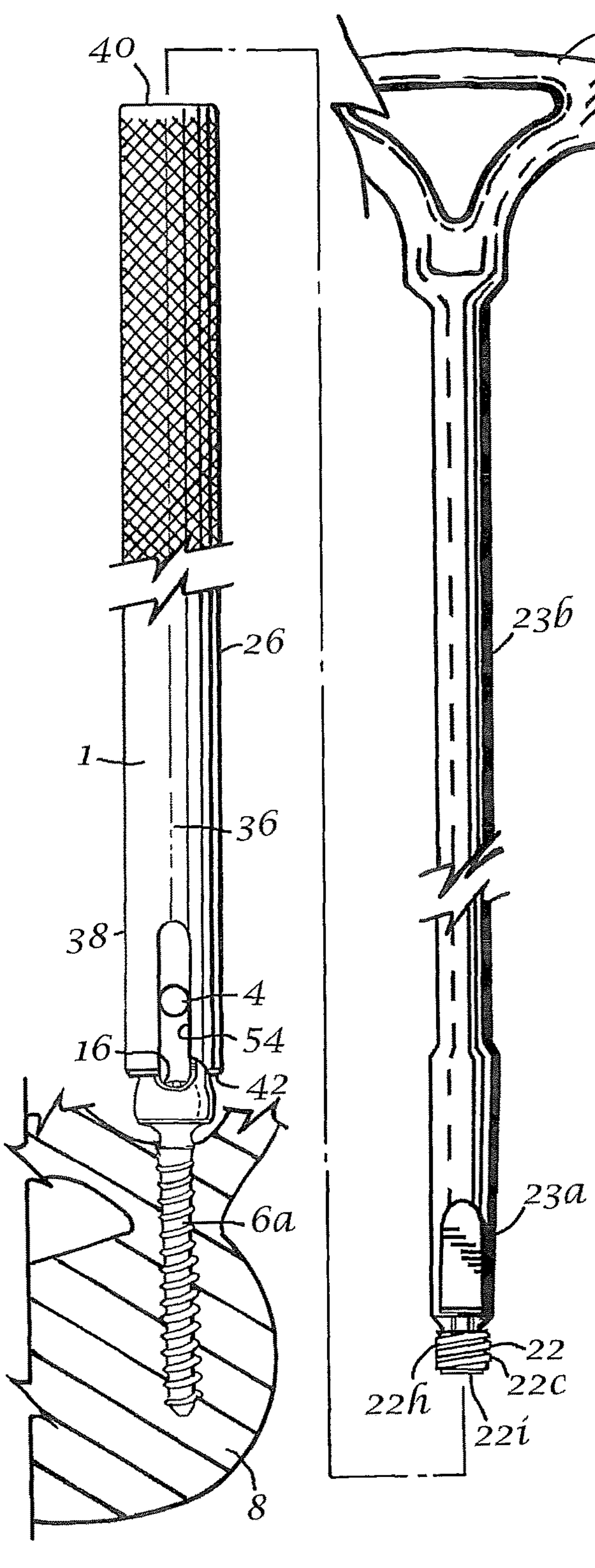
FIG. 13 is a reduced side view of the guide tool of FIG. 1 showing the guide tool attached to the polyaxial bone screw of FIG. 6, including a rod, a closure top adapted for use with the guide tool and the bone screw and also a closure installation tool adapted for use with the guide tool and the bone screw.
Figure 14:
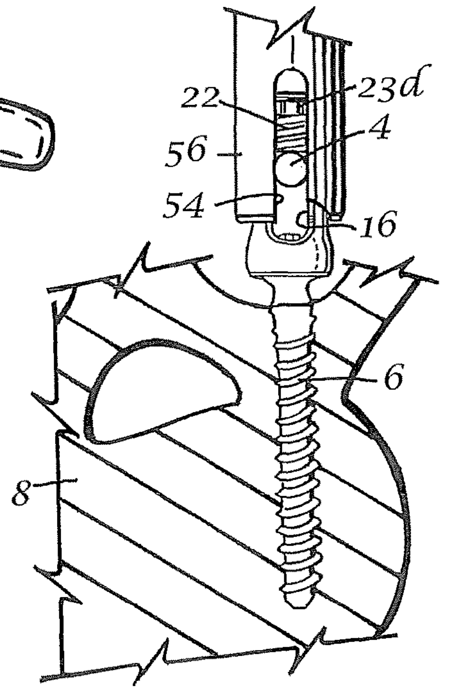
FIG. 14 is a side view of the guide tool of FIG. 13, with portions broken away, illustrating a step of guiding the rod into the bone screw and of installing the closure top.

Referring to FIGS. 4, 5, 13, and 34-35, in the illustrated embodiment, the closure's guide and advancement structure 22*h* has a square form or a square thread type shape. The guide tool's guide and advancement structure 66 allows the closure top 22 to be rotated and the surgeon to develop mechanical advantage to urge or drive the rod 4, while still outside the bone screw head 12, toward and into the bone screw head 12, such as is shown in FIGS. 13-15. Alternatively, this configuration enables pulling the bone screw head 12 around the rod 4 by rotating the closure top 22 in the guide tool 1. This is especially helpful where the rod 4 is bent relative to the location of the vertebra 8 to which the rod 4 is to be attached and is not easily placed in the bone screw head 12 without force and the mechanical advantage provided by the guide and advancement structure 66. In particular, the guide tool's guide and advancement structure 66 is located and positioned to align with the guide and advancement structure 20 on the insides 18 of the bone screw arms 14, as seen in FIGS. 5 and 35 and pass the closure top 22 therebetween while allowing the closure top 22 to continue to rotate and to continuously apply force to the rod 4, so as to seat the rod 4 in the bone screw head 12.

Referring to FIGS. 34-35, in some embodiments, the closure top 22 includes a break off head **22*d* that breaks from the body in a break off region upon the application of a preselected torque, such as about 95 inch-pounds. The break off head 22*d* preferably has a hexagonal cross section faceted exterior that is adapted to mate with a cooperating hex-shaped socket 23*e* (shown in phantom) of the driver head 23*a*. In other embodiments, the closure top 22 may include an imprint 22*d* adapted to cooperate with a flat-head closure driver 23. It is foreseen that different driving heads 23*a* or other methods of driving the closure top 22 can be utilized with certain embodiments of the invention. For example, the closure top 22 may have an axial imprint 22*d* or engagement structure adapted to releasably engage a complementary driving head 23*a* of the closure driver 23**.

As is known in the art, additional tools may be utilized to assemble the implant. For example, a rod pusher (not shown) that has an elongate shaft or rod that is received in and passes through the interior of the guide tool 1, such as the through-bore 44 of the guide tool 1, can be used to engage and urge the rod 4 downward. Alternatively, a pusher or gripper (not shown) of the type that operates outside the guide tool 1 can be utilized.

FIGS. 4-5, 11, 13, 15, and 34-35 illustrate closure installation tools 23 or drivers. Each of the tools 23 has an elongate rod or shaft **23*b* adapted to be received in and pass axially through the guide tool through-bore 44 and a handle 23*c*. The lower end of the rod 23*b* terminates in either a driving engagement structure 23*d*, such as a socket 23*c*, shaped head 23*a* or an imprint engagement structure 23*d*, that is adapted to engage a respective complementary engagement structure of the closure 22**, such as is described above.

Another tool useful in implanting a rod 4 is an antitorque tool (not shown) which is preferably used with the closure installation tool 23 to torque and set the closure top 22, so it is snug against the rod 4, and thereafter break away the break off head **22*d*. The antitorque tool may include a tubular hollow shaft that is sized and shaped to be slidably received over the guide tool 1. The antitorque tool has a lower end that has a pair of diametrically spaced bridges. Each of the bridges is sized and shaped to fit over the rod 4. When in place, the antitorque tool allows a surgeon to counter torque applied by the closure installation tool 23, when applying torque to and breaking away the break off head 22*d***.

In use, the previously described tools are utilized to attach one or more rods 4 to the human spinal column.

The minimally invasive implantation procedure (not shown) is begun by forming a relatively small incision in the skin for each bone screw 6 to be used. The incisions are stretched into a round shape with a circumference equal to or just slightly larger than the guide tools 1. The skin is relatively flexible and allows the surgeon to move the incision around relative to the spine to manipulate the various tools and implants, as required. A drill is utilized to form a guide bore in a vertebra 8 under guidance of non-invasive imaging techniques, which procedure is well known and established. A thin pin or wire **11*a* is inserted in the guide bore, such as for example as is shown in FIG. 11. A bone screw 6 is selected in accordance with the size of the patient's vertebra 8 and the requirements of the spinal support needed. Bone screws 6 having a rotatable or poly axial head 12, such as is shown in FIG. 12, are preferred for the procedure, as they allow relatively easy adjustment of the rod 4 in the guide tools 1 during placement and for movement of tools 1, as described below. The bone screw 6 is also cannulated 11 so as to be receivable over and guided by the pin or wire 11*a* toward the proper position in the associated vertebra 8**.

Before placing the bone screw 6 in the vertebra 8, the bone screw 6 is preferably joined to an associated guide tool 1. This could be done after insertion of the bone screw 6, but it is preferred to assemble both before inserting the bone screw 6. The guide tool 1 is rotatably attached to the bone screw head 12 between the legs 56, using a twist-on procedure, such as is described above and shown in FIGS. 6-9. Namely, the guide tool 1 can be axially rotated ninety degrees relative to the bone screw 6 and the attachment structure 68 aligned with the bone screw's tool engagement structure 21, such as is described above.

A series of bone screws 6 are installed in each vertebra 8 to be attached to the rod 4 by use of a screwdriver or installation tool 51, that has a head **51*a* designed to grip the particular bone screw 6 used and which is also cannulated 51*d* to receive the pin or guide wire 11*a*. For each bone screw 6, an associated guide tool 1 extends through the skin. A guide tool 1 is located at each end of the series of bone screws 6 as well as on each intermediate bone screw 6. The guide tools 1 are turned or rotated so the through-slots 54 face one another so as to provide a continuous path adapted to receive the rod 4** therethrough.

The rod 4 is then inserted diagonally through one of the end skin incisions so that a first rod end passes through the through-slots 54 in the guide tools 1. Back muscle tissue separates easily here to allow the insertion of the rod 4 and can be further separated by finger separation or cutting through one of the incisions, if required.

Once the rod 4 is positioned in the guide tools 1, a closure top 22 and closure driver 23 are utilized to push the rod 4 in each guide tool 1 toward the bone screw 6 associated with the guide tool 1 until the rod 4 is seated in the bone screw U-shaped channels 16, such as is shown in FIGS. 5, 13-15 and 35. When the rod 4 is at the bottom of the guide tools 1, such as seen in FIG. 15, the guide tools 1 can be manipulated to further align the bone screw heads 12 relative to the rod 4 prior to tightening and torquing the closure tops 22.

Because the rod 4 is normally bent and/or the vertebrae 8 do not align properly, the rod 4 must normally be biased into the bone screw heads 12. This is accomplished by using the closure installation tool 23 in the manner illustrated in FIGS. 5, 13-15 and 35, as is described above. In particular, the closure installation tool 23 has a socket or imprint engagement structure **23*d* that grips the closure top 22. The installation tool 23 with closure top 22 therein is placed in the guide tool's elongate through-bore 44, or top to bottom channel, through the top opening 46 in guide tool 1. The closure top 22 is then driven under manual control of the surgeon by use of the installation tool 23 toward the rod 4. Near the bottom end 42 of the guide tool 1, such as near the bottom opening 48 of guide tool 1, the guide and advancement structure 22***h* of the closure top 22 engages the guide tool's helical wound guide and advancement structure 66, and the tool 23 and closure top 22 are rotated so as to drive the closure top 22 downward against the rod 4 and to urge the rod 4 into the bone screw U-shaped channel 16. At the bottom of the guide tool 1, the closure top guide and advancement structure 22*h* engages and begins to mate with the guide and advancement structure 20 on the arms 14 of the respective bone screw 6, and continued rotation of the tool 23 drives the rod 4 downward and into engagement with the bone screw shank upper portion 10*a*, so as to snug against and frictionally lock the shank 10 in position relative to the bone screw head 12. It is noted that in some embodiments, the bone screw 6 includes a pressure insert located between the rod 4 and the shank upper portion 10*a*.

Once all of the closure tops 26 are in final seating position in respective bone screws 6 and the surgeon is satisfied with the position of all of the elements, the antitorque tool (not shown) is mounted over each guide tool 1 with the bridges straddling the rod 4 to prevent rotation. The closure installation tool 23 is inserted in the associated guide tool 1 and engaged with the closure tops 22. By cooperative use of the anti-torque tool and the closure driver 23, a preselected torque is manually applied to the closure top 22. If the closure top 22 includes a break-off head 22*d*, the break-off head 22*d* is removed during this procedure.

Figure 24:
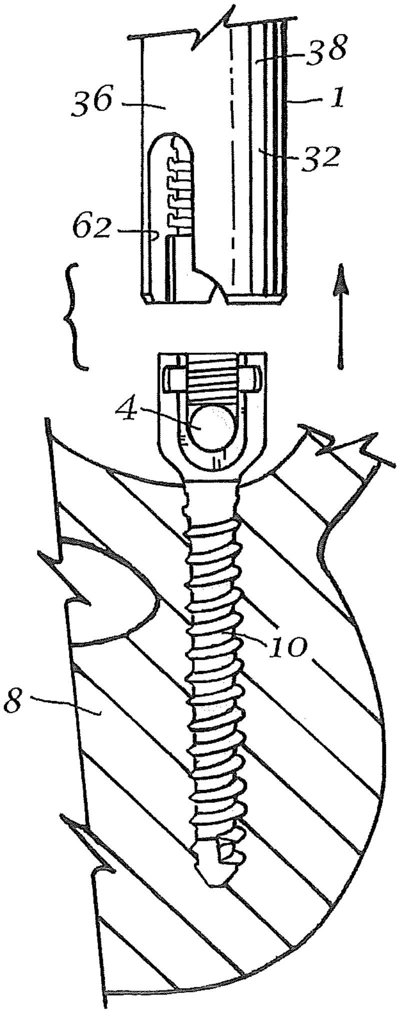
FIG. 24 is a side view of the guide tool and monoaxial bone screw of FIG. 23 illustrating a further step in detaching the guide tool from the monoaxial bone screw.
Figure 25:
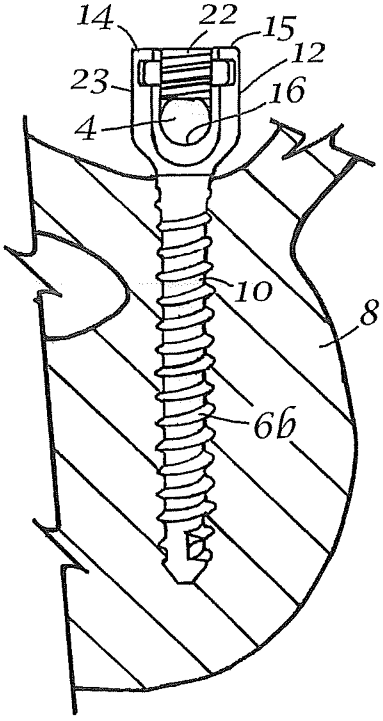
FIG. 25 is a side view of the monoaxial bone screw of FIG. 24, with the rod and closure top installed, and after the guide tool has been detached.
Figure 26:
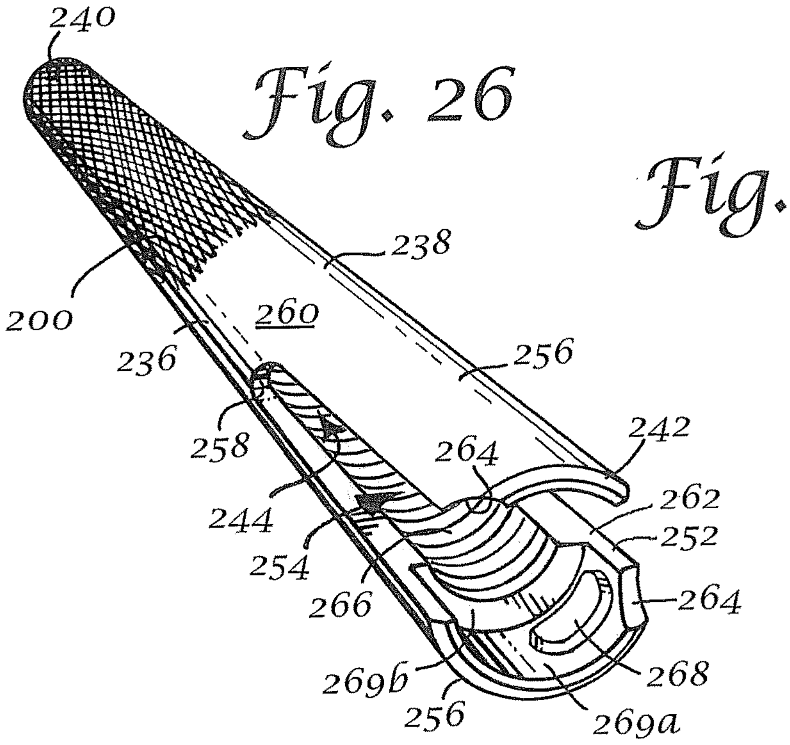
FIG. 26 is perspective view of a guide tool for percutaneously implanting a rod in a patient, in a second embodiment.

The guide tools 1 are then detached from the respective bone screws 6, using the twist-off procedure described above. Namely, each guide tool is rotated ninety degrees clockwise (see FIGS. 16-17 and 23-25) so that the recess 64 straddles the rod 4 (see FIGS. 16 and 23) to allow respective tool and screw attachment structure 68 and 21 to detach or disengage from one another. The guide tool 1 is then pulled axially upward away from the bone screw 6, such as is shown in FIGS. 17 and 24, and from the incision in the skin, after which the incision is closed. It is foreseen that the guide tool 1 and the bone screw 6 may be configured or adapted such that the guide tool 1 is mountable onto the bone screw with a clockwise twist-on procedure and disconnectable with a counter-clockwise twist-off procedure.

FIGS. 26-35 illustrate a guide tool 200 in a second embodiment. The guide tool 200 is similar to the guide tool 1 of the first embodiment, the description of which is incorporated herein by reference. Accordingly, structures corresponding between the two embodiments have been numbered similarly.

Figure 27:
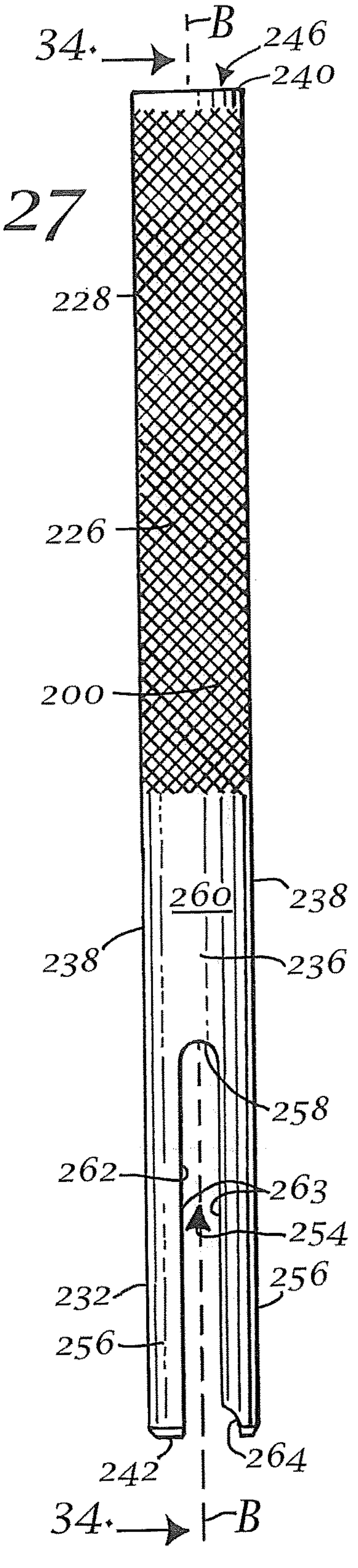
FIG. 27 is a reduced side view of the guide tool of FIG. 26.
Figure 28:
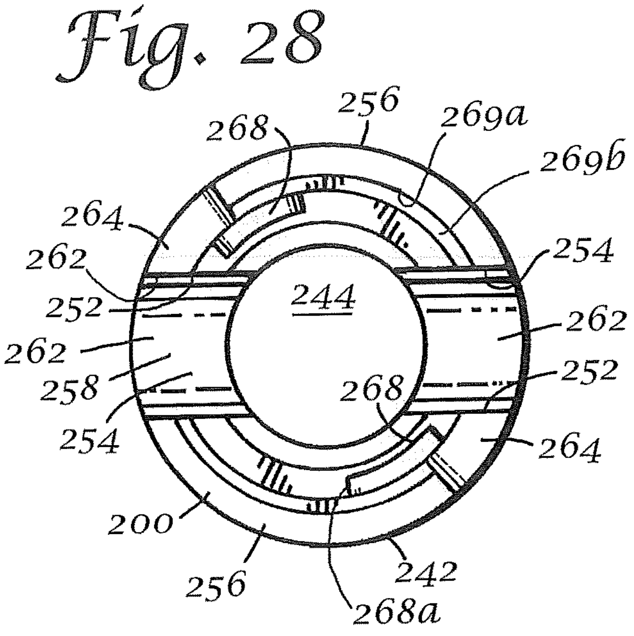
FIG. 28 is an enlarged bottom view of the guide tool of FIG. 26.
Figure 29:
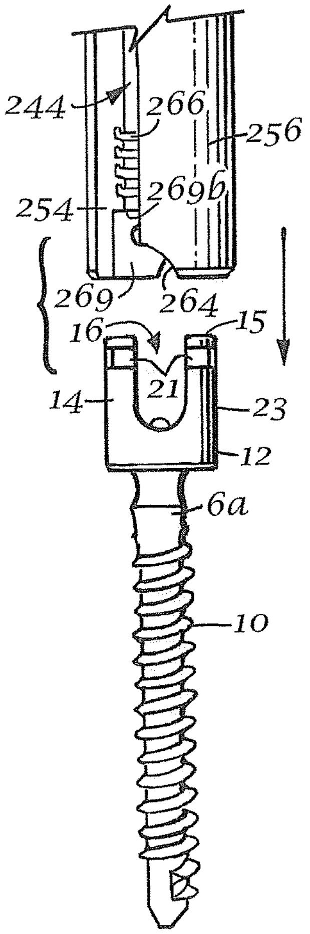
FIG. 29 is an enlarged side view of the guide tool of FIG. 26, with portions broken away, illustrating an initial step in attaching the guide tool of FIG. 26 to a polyaxial bone screw adapted for use with the guide tool of FIG. 26.

In a second embodiment, the guide tool 200 includes an elongate body 226 having an upper handle portion 228, an intermediate or middle portion 230, a lower or bottom portion 232 and a longitudinally extending axis B. The body 226 is generally cylindrical and includes front and rear walls 236 and side walls 238, and top and bottom ends 240 and 242, respectively. A through-bore 244 extends longitudinally through the body 226 and joins a first, upper or top opening 246 located at the tool top end 240 with a second, lower or bottom opening 248 located at the tool bottom end 242. The through-bore 244 is adapted to receive a closure driver 23, a closure 22 and a bone screw driver 51 therein. In preferred embodiments, the through-bore 244 is coaxial with the longitudinal axis B, such as is shown in FIG. 27.

At the lower end 242, the front and rear walls 236 each include an upwardly extending cutout 252. The cutouts 252 extend upwardly from the bottom opening 248 to or near to the body middle portion 236. For example, the cutouts 252 may extend upwardly a length of about 0.25-percent to about 0.5-percent of the total length of the guide tool 200, so as to provide legs 256 of increased or extended length relative to the legs 56 of the first guide too 1. This increased leg length can provide additional flexibility to the legs 256, so as to enable the legs 256 to expand apart and snap onto the bone screw 6. Also, given the tight working area of the minimally invasive incision, the extra length of the cutouts 252, as compared with the cutouts 52 of the first embodiment, provides additional space for passing or installing a rod 4 simultaneously through the patient's skin and through the cutouts 252. This makes the installation somewhat easier than with the guide tool 1 of the first embodiment and may reduce the amount of tissue resection required for the surgical procedure.

The cutouts 252 define a through-slot 254 and the pair of spaced opposed legs 256. Each cutout 252 includes an upper slot surface 258. The body outer surface 260 is joined with the through-bore inner surface 250 by spaced opposed openings 262. The openings 262 include sides 263 that run substantially parallel with one another and are spaced a distance equal to or slightly great that a diameter of the rod 4. This sizing allows the rod 4 to be smoothly threaded through the through-slot 254, optionally while holding the rod 4 in a somewhat more vertical orientation relative to the surgical incision. As a result, a smaller incision can be used for the surgical procedure.

The legs 256 each include a rod-abutment recess, cut-out or relief 264 that is sized and shaped to allow the surgeon to perform the twist-off maneuver described above, after the rod 4 has been installed in that bone screw 6.

As shown in FIG. 34, the guide tool inner surface 250 includes a helically wound guide and advancement structure 266 substantially similar to the guide and advancement structure 66 of first guide tool 1. Generally, the guide and advancement structure 266 runs from above the cutout upper surface 258 to the mating portion 269 at the lower end 232 of the guide tool body 226. However, it is foreseen that the guide and advancement structure 266 may begin somewhat higher or lower than is shown in the figures. For example, it is foreseen that the guide and advancement structure 266 may extend to nearly the top 240 of the guide tool 200, or, alternatively, may begin below the upper slot surface 258. The guide and advancement structure 266 is adapted to cooperatively rotatably mate with the closure's guide and advancement structure 22*h*. As shown in FIG. 35, when the guide tool 200 is mounted on the bone screw 6, the guide tool's guide and advancement structure 266 is configured to align with the bone screw's guide and advancement structure 20, such that the closure top 22 can be smoothly rotatably passed between the two structures.

Figure 30:
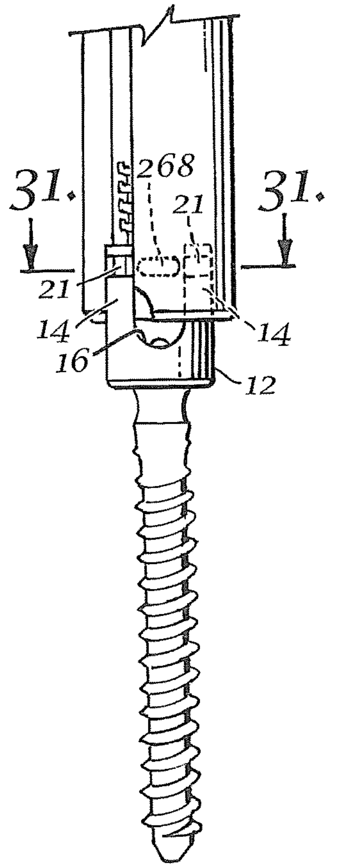
FIG. 30 is a side view of the guide tool and polyaxial bone screw of FIG. 29 illustrating an intermediate step in attaching the guide tool to the polyaxial bone screw, wherein the guide tool through-slot is not yet aligned with the bone screw U-shaped channel.
Figure 32:
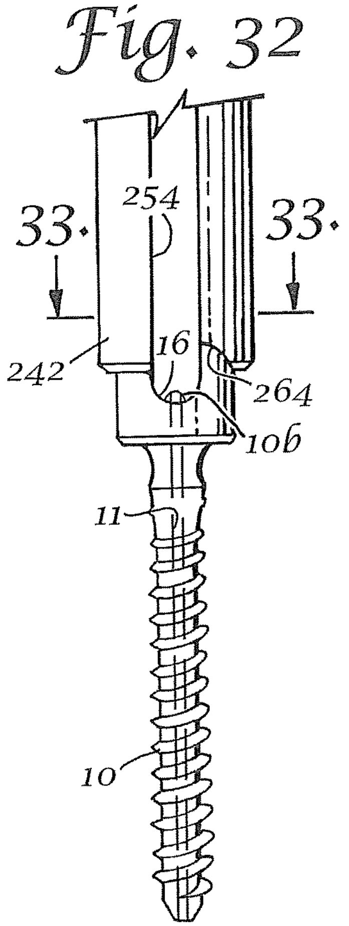
FIG. 32 is a side view of the assembly of FIG. 30 illustrating the guide tool attached to or mounted on the polyaxial bone screw, wherein the guide tool through-slot is substantially aligned with the bone screw U-shaped channel.
Figure 31:
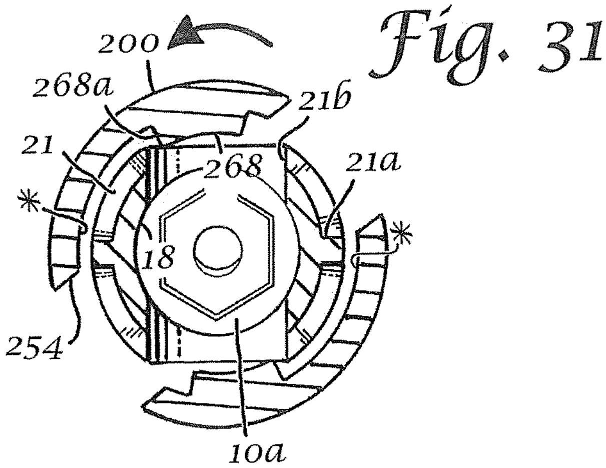
FIG. 31 is an enlarged cross-sectional view of the assembly of FIG. 30 taken along the line 31-31 of FIG. 30 illustrating the an initial step in aligning and engaging the guide tool bone screw attachment structure with the complementary bone screw tool engagement structure.

Referring now to FIGS. 29-33, as shown in FIGS. 30 and 31, when initially mounting the guide tool 200 on top of the bone screw head 12, the guide tool 200 is placed on top of the bone screw head 12 in such an orientation that the guide tool's screw abutment surfaces 269 contact the bone screw arm top surfaces 15 but the guide tool's through-slot 254 and the bone screw's U-shaped channel 16 are not aligned. When in this configuration or position, guide tool's lozenge-shaped bone screw attachment structure 268 (shown in phantom in FIG. 30) is vertically aligned with the bone screw's tool engagement structure 21 (shown in phantom in FIG. 30).

As shown in FIG. 31, in the illustrated embodiment, the guide tool engagement structure 276 is generally shaped like a rectangle with rounded corners or like a lozenge. The bone screw's tool engagement structure 21 is a complementary sized and shaped channel or slot adapted to slidingly receive therein and cooperatively mate with the attachment structure 268, such that the two structures 268 and 21 snugly engage one another. The opening 21*b* of the engagement structure 21*a* is contiguous with the U-shaped channel 16, such that the counter-clockwise rotation of the guide tool 200 with respect to the bone screw head 12 slides the attachment structure 268 into the tool engagement structure 21, until the stops 268*a* and 21*a* abut one another. Alternatively shaped structures 268 and 21 are foreseen, so long as the structures 268 and 21 are complementary to one another and cooperatively reversibly engage, or interlock, with one another using a twist-on motion.

It is noted that when viewed from the side 238, the attachment structure 268 is located very closed to the left-hand edge of the respective leg 256, just above the rod-abutment surface 264. This arrangement of structures enables the guide tool 200 to be twisted onto the bone screw 6 using a counter-clockwise turn (compare FIGS. 31 and 33). It is foreseen that the guide tool's bone screw attachment structure 268 and the rod-abutment surface 264 could be located on the opposite or right-hand side to the leg 256, as denoted by the asterisk (*) in FIG. 31, such that the guide tool 200 would be twisted onto the bone screw 6 using a clockwise turn. Additional alternative configurations are foreseen.

Figure 33:
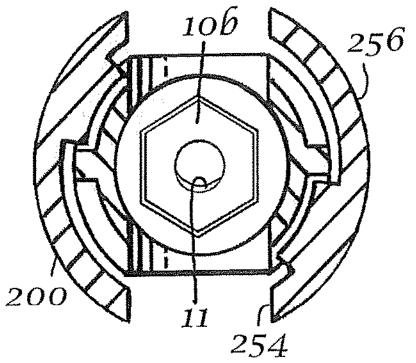
FIG. 33 is an enlarged cross-sectional view of the assembly of FIG. 32 taken along the line 33-33 of FIG. 32 illustrating the guide tool bone screw attachment structure reversibly engaged with the bone screw tool engagement structure.

Referring again to FIGS. 29-33, once the guide tool's attachment structure 268 and the slot or bone screw's engagement structure 21 are aligned (see FIGS. 30 and 31) the guide tool 200 is rotated about 90-degrees counter-clockwise, relative to the bone screw 6. During this twisting movement, the attachment structure 268 enters and engages the engagement structure 21, such as is shown in FIG. 33.

As noted above, the bone screw engagement structure 21 includes a stop surface 21*a* that during the twist-on maneuver come into contact with or engagement with a first or forward surface 268*a* of the attachment structure 268, such that the guide tool 200 cannot be rotated farther. When the forward surface 268*a* engages the stop surface 21*a*, the guide tool's through-slot 254 is substantially aligned with the bone screw's U-shaped channel 16. Additionally, when forward surface 268*a* and the stop surface 21*a* are in engagement, the tool's guide and advancement structure 266 is correctly aligned with the bone screw guide and advancement structure 20, so as to provide a smooth transition therebetween, such that the closure top 22 can be installed into the bone screw 6 without binding up (see FIG. 35).

FIGS. 36-43 illustrate a guide tool 300 in a third embodiment. The third guide tool 300 is substantially similar to the guide tools 1 and 200 of the first and second embodiments, the descriptions of which are incorporated herein by reference. Therefore the guide tool 300 is numbered in a similar manner to guide tools 1 and 200. In particular, the guide tool 300 of the third embodiment includes the following structures, portions or features: a body 326 that includes an upper handle portion 328, an intermediate portion and a lower portion 332, front and back walls 336, side walls 338, top and bottom ends 340 and 342 respectively, a through-bore 344 that is coaxial with the longitudinal axis C and extends from a top opening 346 located at the top end 340 to a bottom opening 348 located at the bottom end 342. The through-bore 344 includes an inner surface 350. Cut-outs 352 in the front and back walls 336 form a through-slot 354 that extends longitudinally upward from the bottom opening 348 and is joined with the through-bore 344. The through-slot 354 also divides the lower portion 332 of the body 326 into a pair of spaced opposed legs 356. The through-slot 354 includes an upper surface 358 and openings 362. The openings 362 join the through-bore inner surface 350 with the body outer surface 360. Similar to the guide tools 1 and 200 of the first and second embodiments, the body lower portion 332 includes a rod-abutment relief 364 that is adapted to straddle a rod 4 during a twist-off procedure, such as is described above. The guide tool 300 also includes a guide and advancement structure 366 adapted for use with a closure top 22, a radially inwardly facing bone screw attachment structure 368 with at least one camming surface 368*b*, and a mating chamber 369 for engaging the bone screw 6. The mating chamber 369 includes a chamber inner surface 369*a* and screw abutment surfaces 369*b* similar to those described with respect to guide tool's 1 and 200.

The bone screw attachment structure 368 of the guide tool 300 is substantially different from the attachment structures 68 and 268 of the first and second guide tool 1 and 200, respectively. Namely, instead of the having an attachment structure that is generally perpendicularly oriented relative to the longitudinal axis, such as the attachment structure 268, the third guide tool's radially inwardly facing bone screw attachment structure 368 is an inwardly extending or facing caming structure with caming surfaces 368*b*. As is most easily seen in FIGS. 38 and 42, the guide tool's bone screw attachment structure 368 is slanted relative to the longitudinal axis C. In particular, the attachment structure 368 is a sloped rectangular structure with rounded corners, wherein the structure 368 slants upwardly from the edge of the respective leg 356 toward the screw abutment surface 39*b* of the tool's mating chamber 369.

As shown in FIGS. 40-43, the bone screw 6 is adapted to cooperatively engage the guide tool 300. Accordingly, the bone screw's tool engagement structure 21 sized and shaped to cooperate with the guide tool's bone screw attachment structure 368. In the illustrated embodiment, the tool engagement structure 21 is a partially helically wound slot or channel with upper and lower openings 21*b* and 21*c*, respectively, and at least one caming surface 21*d*. The tool engagement structures 21 wraps around the outer surfaces of the respective arms 14 such that the upper openings 21*b* are located closer to the respective arm top surfaces 15 than are the lower openings 21*c*. The bone screw's tool engagement structure 21 is sized and shaped to slidingly receive the guide tool's bone screw attachment structure 368 therein using a counter-clockwise twist-on maneuver. For example, when the guide tool 300 is mounted on the bone screw 6, counter-clockwise rotation of the guide tool 300 with respect to the bone screw head 12 slides the attachment structure 368 into the upper opening 21*b* of the engagement structure 21. Upon entry of the attachment structure 368 into the engagement structure 21, the guide tool's screw abutment surfaces 369*b*, of the tool's mating chamber 369, are spaced from the bone screw's arm upper surfaces 15. Additionally, the caming surfaces 368*b* and 21*d* engage one another. Upon continued clockwise rotation of the guide tool, the caming surfaces 368*b* and 21*d* cooperate to lock the guide tool's mating chamber 369 about the upper portions of the bone screw arms 14. When the guide tool's through-slot 354 is substantially aligned with the bone screw's U-shaped channel 16, the surfaces 369*b* and 15 engage one another, whereby additional counter-clockwise rotation of the guide tool 300 is prevents. However, it is foreseen that if over-rotation occurs, the guide tool 300 can be rotated clockwise to align the through-slot 354 and the U-shaped channel 16. Disconnection of the guide tool 300 from the bone screw 6 is generally accomplished using a clockwise twist-off procedure, such as described elsewhere herein. It is foreseen that the guide tool 300 and the bone screw 6 can be configured and arranged for a clockwise twist-on procedure and a counter-clockwise twist-off procedure. It is also foreseen that the guide tool legs 356 may include sufficient flexibility enable some splaying apart, so as to assist in mounting the tool 300 on the bone screw 6.

FIGS. 44-51 illustrate a guide tool 400 in a fourth embodiment. The fourth guide tool 400 is substantially similar to the guide tools 1, 200 and 300 of the first, second and third embodiments, the descriptions of which are incorporated herein by reference. Therefor the guide tool 400 is numbered in a manner similar to the numbering of the guide tools 1, 200 and 300. In particular, the guide tool 400 of the fourth embodiment includes the following structures, portions or features: a body 426 that includes an upper handle portion 428, an intermediate portion and a lower portion 432, front and back walls 436, side walls 438, top and bottom ends 440 and 442 respectively, a through-bore 444 that is coaxial with the longitudinal axis D and joins the top opening 446 located at the top end 440 with the bottom opening 448 located at the bottom end 442. The through-bore 444 includes an inner surface 450. Cut-outs 452 in the front and back walls 436 form a through-slot 454 that extends longitudinally upward from the bottom opening 448 and is joined with the through-bore 444. The through-slot 454 also divides the lower portion 432 of the body 426 into a pair of spaced opposed legs 456. The through-slot 454 includes an upper surface 458 and openings 462. The openings 462 join the through-bore inner surface 450 with the body outer surface 460. In contrast to the guide tools 1, 200 and 300 of the first, second and third embodiments, the body lower portion 432 does not include a rod-abutment relief. Instead, as described in greater detail below, the guide tool's mating chamber 469 is adapted such that a rod-abutment relief is not required for disconnection of the guide tool 400 from and attached bone screw. The guide tool 400 includes a guide and advancement structure 466 adapted for use with a closure top 22, a radially inwardly facing bone screw attachment structure 468 and a mating chamber 469 for engaging the bone screw 6. The mating chamber 469 includes a chamber inner surface 469*a* and screw abutment surfaces 469*b*.

As is most easily seen in FIGS. 44 and 46-51, the guide tool's bone screw attachment structure 468 is located on the mating chamber's inner surface 469*a* approximately equidistant from each of the cutouts 4521 that define the legs 456. Additionally, the attachment structure 468 is located very near to or adjacent to the lower opening 468 or the bottom 442 of the respective leg 456. Consequently, the tool's mating chamber 469 is very short relative to the mating chambers 69, 269 and 369 described above.

Figure 47:
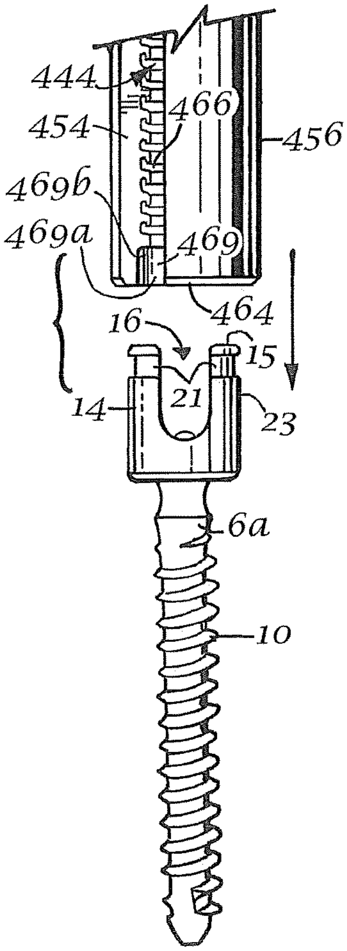
FIG. 47 is an enlarged side view of the guide tool of FIG. 44, with portions broken away, illustrating a first step in attaching the guide tool of FIG. 44 to a polyaxial bone screw adapted for use therewith.
Figure 48:
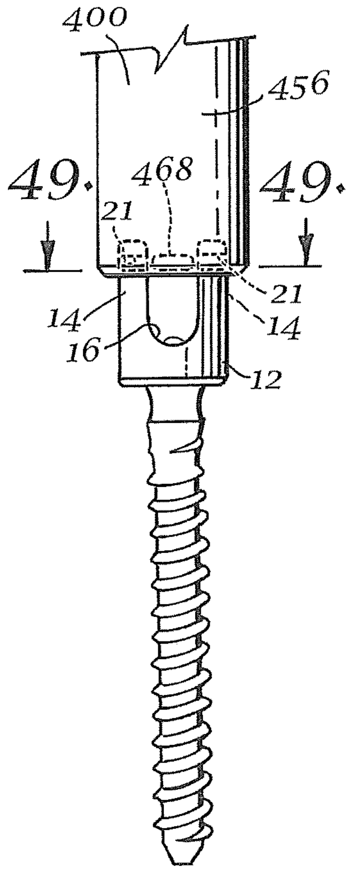
FIG. 48 is a side view of the guide tool of FIG. 47 illustrating a further step in attaching the guide tool to the polyaxial bone screw, wherein the guide tool through-slot is not yet aligned with the bone screw U-shaped channel.
Figure 50:
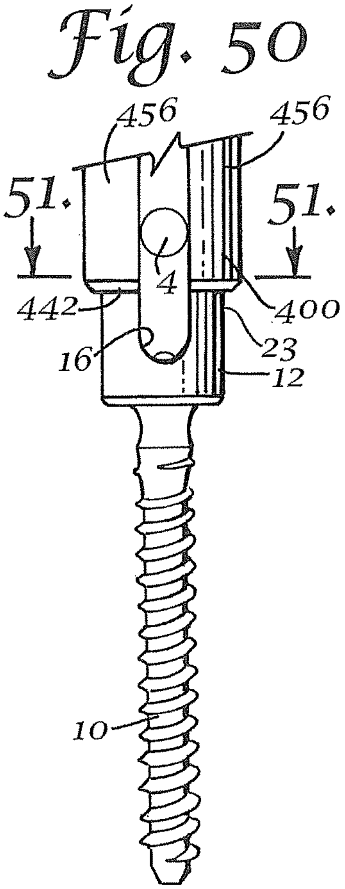
FIG. 50 is a side view of the assembly of FIG. 48 illustrating attachment of the guide tool to the polyaxial bone screw of FIG. 47, wherein the guide tool through-slot is substantially aligned with the bone screw U-shaped channel.
Figure 49:
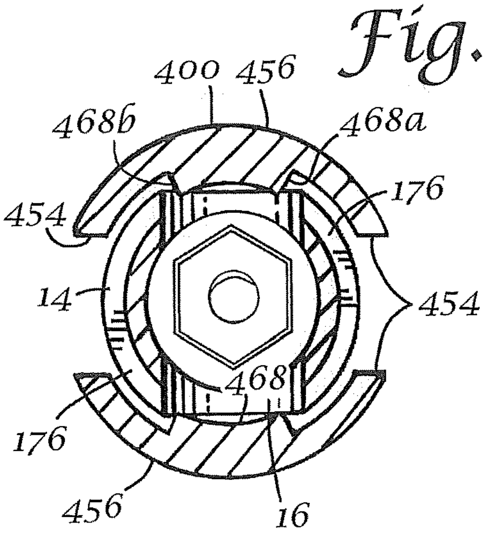
FIG. 49 is an enlarged cross-section of the assembly of FIG. 48 taken along line the 49-49 of FIG. 48 illustrating an initial step in aligning and engaging the guide tool bone screw attachment structure with the complementary bone screw tool engagement structure.
Figure 51:
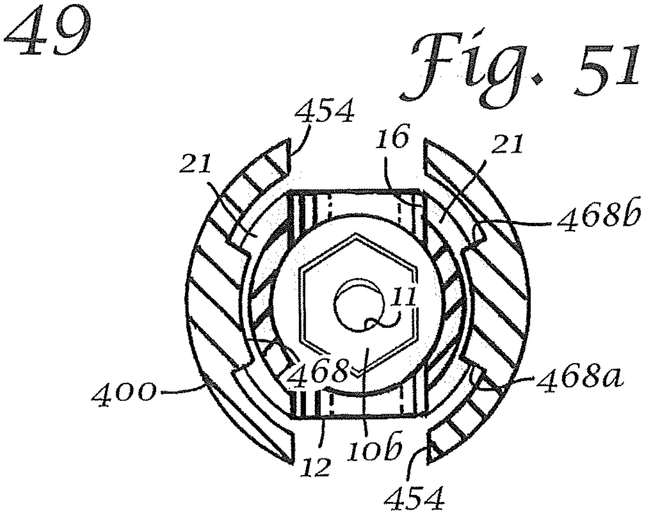
FIG. 51 is an enlarged cross-section of the guide tool and bone screw of FIG. 50 taken along line the 51-51 of FIG. 50 and showing reversible engagement between the guide tool bone screw attachment structure and the bone screw tool engagement structure.
Figure 52:
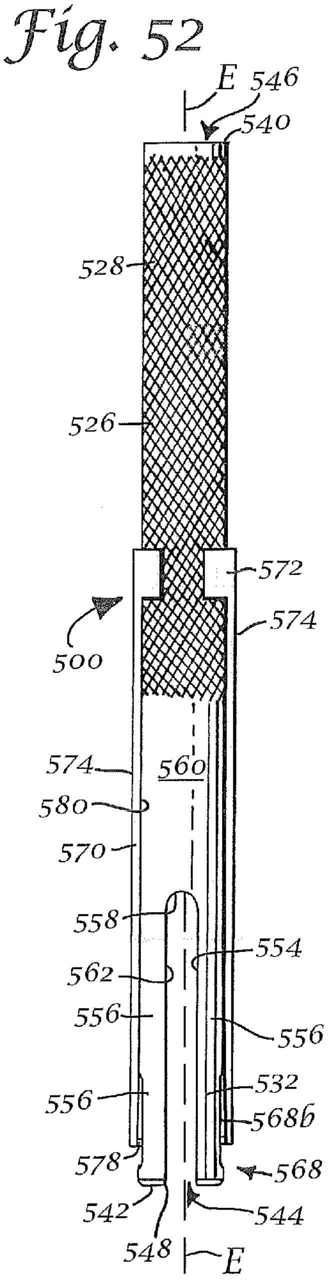
FIG. 52 is side view of a guide tool for percutaneously implanting a rod in a patient, in a fifth embodiment.

As shown in FIGS. 47-48, the bone screw's tool engagement structure 21 is adapted to cooperate with tool's screw attachment structure 468. Accordingly, the bone screw's tool engagement structure 21 is a radial groove, slot or notch that wraps around the outer surfaces of the arms 14. The tool engagement structure 21 is oriented substantially perpendicular to the bone screw arms 14, such that it runs substantially parallel with the arm upper surfaces 15. Further, the tool engagement structures 21 are located so as to be vertically spaced very close to or adjacent to the upper surface 15. As a result, the tool's mating chamber 469 engages only a small portion of the arms 14.

Since the guide tool's bone screw attachment structure 648 and the bone screw's tool engagement structure 21 are substantially perpendicular to the longitudinal axis D of the guide tool 400, such as when the tool 400 is mounted on the bone screw 6, the guide tool 400 is rotatable in either of the clockwise and counter-clockwise directions relative to the bone screw head 12, in a twist-on procedure. Similarly, the guide tool 400 can be rotated rotatable in either of the clockwise and counter-clockwise directions in a twist-off procedure. Regardless of the direction tool rotation of the twist-on procedure, the guide tool 400 is rotated about 90-degrees relative to the bone screw head 12, so as to align the guide tool's through slot 454 with the bone screw's U-shaped channel 16, and the implantation procedure can be continued as is described above.

FIGS. 52-59 illustrate a guide tool 500 in a fifth embodiment. The fifth guide tool 500 is similar to the guide tools 1, 200, 300 and 400 of the first, second, third and fourth embodiments, the descriptions of which are incorporated herein by reference. Therefore the guide tool 500 is numbered in a manner similar to the numbering of guide tools 1, 200, 300 and 400. In particular, the guide tool 500 of the fifth embodiment includes the following structures, portions or features: a body 526 that includes an upper handle portion 528, an intermediate portion and a lower portion 532, front and back walls 536, side walls 538, top and bottom ends 540 and 542 respectively, a through-bore 544 that is coaxial with the longitudinal axis E and extends from a top opening 546 located at the top end 540 to a bottom opening 548 located at the bottom end 542. The through-bore 544 includes an inner surface 550. Cut-outs 552 in the front and back walls 536 form a through-slot 554 that extends longitudinally upward from the bottom opening 548 and is joined with the through-bore 544. The through-slot 554 also divides the lower portion 532 of the body 526 into a pair of spaced opposed legs 556. The through-slot 554 includes an upper surface 558 and openings 562. The openings 562 join the through-bore inner surface 550 with the body outer surface 560. The guide tool 500 also includes a guide and advancement structure 566 adapted for use with a closure top 22, a radially inwardly facing bone screw attachment structure 568, which is described in greater detail below, and a mating chamber 569 for engaging the bone screw 6. The mating chamber 569 includes an inner chamber surface 569*a* and screw abutment surfaces 569*b*. Similar to the guide tool 400 of the fourth embodiment, the body lower portion 532 does not include a rod-abutment relief.

Figure 53:
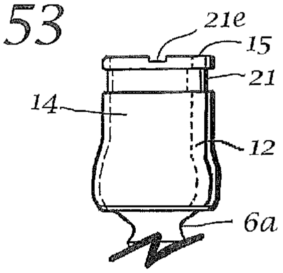
FIG. 53 is a side view of a polyaxial bone screw adapted for use with the guide tool of FIG. 52, with portions broken away.
Figure 54:
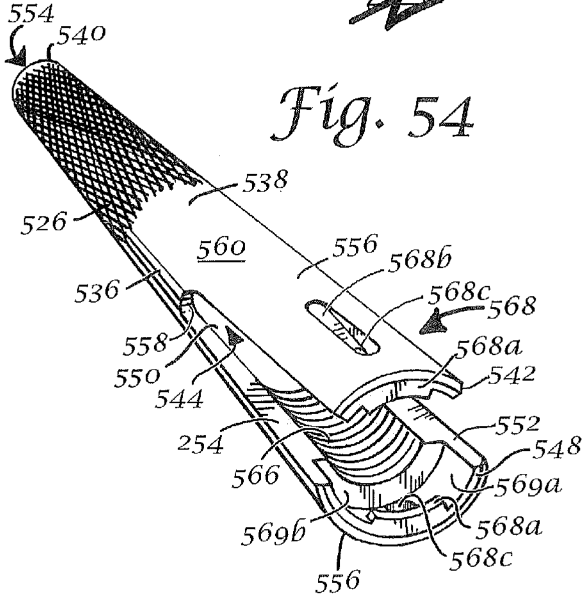
FIG. 54 is an enlarged perspective view of a first portion of the guide tool of FIG. 52.
Figure 55:
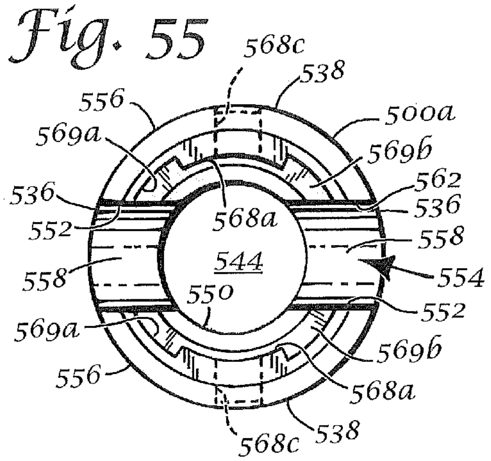
FIG. 55 is an enlarged bottom view of the guide tool first portion of FIG. 54.
Figure 56:
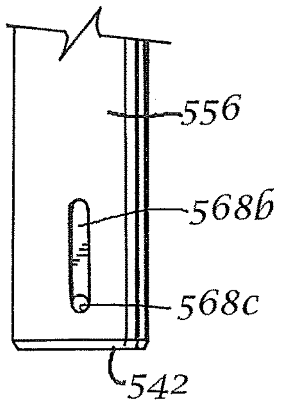
FIG. 56 is a side view of the guide tool first portion of FIG. 54, with portions broken away.

Referring now to FIG. 53, a bone screw, such as but not limited to a polyaxial bone screw 6*a*, for use with the guide tool 500 includes a tool attachment structure 21 that is similar to that of the bone screw 6*a* descried with reference to FIGS. 47 through 51. For example, the tool engagement structure 21 includes a radial groove, slot or notch that wraps around the outer surface of the bone screw arms 16, such that cross-sections of the slots, which is taken perpendicular to the longitudinal axis of the head 12, are generally semi-circular, crescent-shaped or C-shaped. Additionally, the tool engagement structure 21 for use with the guide tool 500 includes a radially extending slot or notch 21*e* in the top surface 15 of each of the arms 14. For example, the slot 21*e* extends radially outward from the U-shaped channel 16 to the outer surface of the respective arm 14. As is described below, the slot 21*e* engages a portion of the guide tool 500, to prevent twisting of the bone screw head 12 relative to the guide tool 500, which the bone screw 6*a* and the guide tool 500 are engaged together. The slot 21*e* shown in FIG. 53 is generally shallow. However, it if foreseen that the slot 21*e* may be deeper than depicted, or the bone screw's tool engagement structure 21 may include additional or alternative structures.

Referring now to FIGS. 52 through 59, the guide tool 500 includes a multi-part bone screw attachment structure 568. In particular, the bone screw attachment structure 568 includes a an attachment member 568*a*, a ramp member

568*b* and a pin-receiving bore 568*c*. The attachment member 568*a* is shelf-like or shoulder-like structure located on the inner surface of the mating chamber 569, such that the attachment member 568*a* extends radially inwardly, toward the longitudinal axis E. The ramp member 568*b* is located on the exterior surface of a respective leg 556. The ramp member 568*b* runs parallel with the longitudinal axis E and slopes inwardly when moving from the tool upper opening 546 toward the bottom opening 548. The ramp member 568*b* terminates with the pin-receiving bore 568*c*, which is generally perpendicular to the longitudinal axis E and joins the ramp member 568*b* with the interior surface of the mating chamber 569. It is foreseen that the pin-receiving bore 568*c* may also be slopes, so as to not be perpendicular to the longitudinal axis E. The pin-receiving bore 568*c* is sized and shaped to receiver therein or there-through a pin or finger member of the guide tool 500, to cooperate with the slot 21*e* and thereby prevent rotation of the guide tool 500 with respect to the bone screw head 12, such as is described below.

The guide tool 500 also includes a tong-like sleeve member 570 that is received over the body 526 and reversibly slidable along the axis E. The sleeve member 570 includes an upper collar portion 572 with a pair of spaced opposed flex arms 574 that extend longitudinally downward from the collar portion 572. The flex arms 574 are inwardly biased. At the lower end 576 of each flex arm 574 is an inwardly extending pin or finger member 578, such as is mentioned above. The finger members 578 extend inwardly from the inner surfaces of the respective flex arms 574 along axis F.

When the sleeve member 570 is received over the guide tool body 526, the inner surfaces 580 of the flex arms 574 frictionally engage the respective outer surfaces of the legs 556. Further, each of the inwardly biased flex arms 574 flexes into respective ramp member 568*b*.

Figure 58:
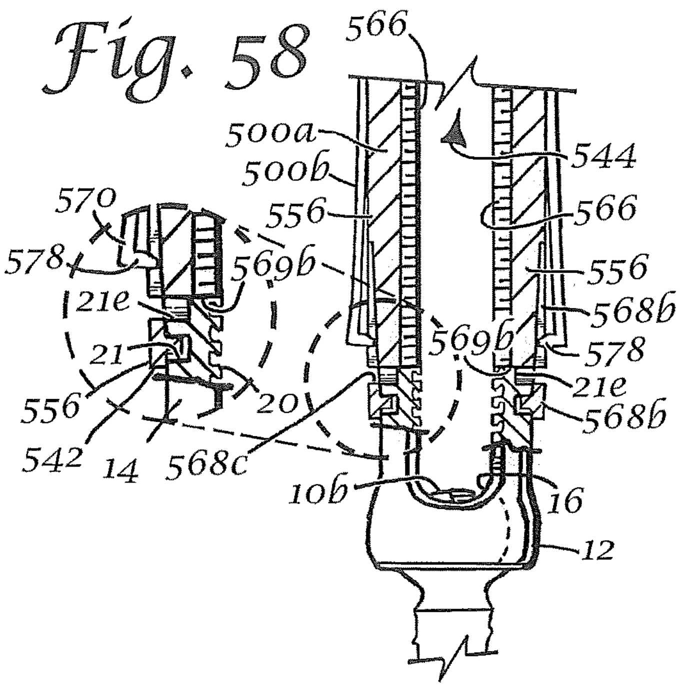
FIG. 58 is a partial cross-sectional view of the guide tool of FIG. 52 taken along line 58-58 of FIG. 57, and illustrating an initial step in attaching the guide tool to the polyaxial bone screw of FIG. 53.
Figure 57:
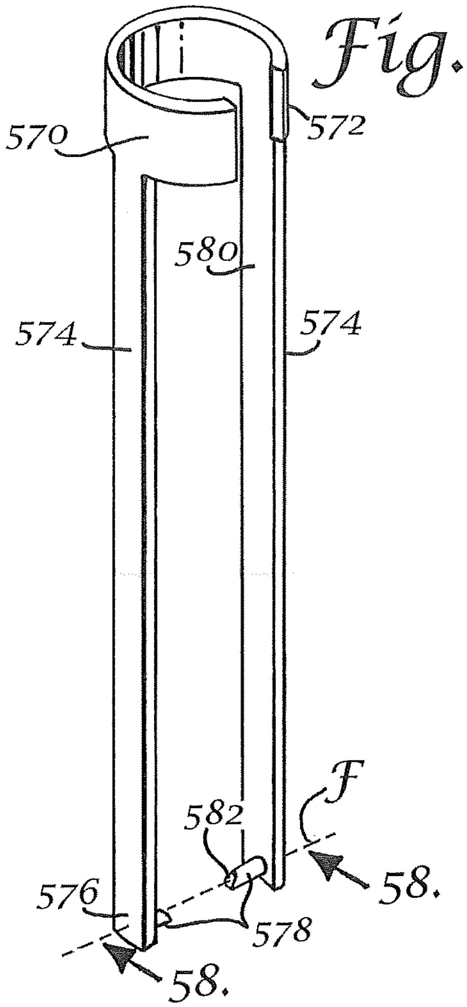
FIG. 57 is an enlarged perspective view of a second portion of the guide tool of FIG. 52.

To mount the guide tool 500 on the bone screw head 12, the guide tool body 526 is reversibly engages with the bone screw arms 14, such as is described above with respect to the fourth guide tool 400, using a twist-on movement, such as is described above. FIG. 58 illustrates the relationship of the guide tool body 526 to the bone screw arms 14, when the two structures are reversibly engaged. In particular, the guide tool shelf member 568*a* is slidingly engaged in the bone screw slot 21. In some embodiments, a lip-like portion of the guide tool bottom end 542 extends downwardly on the exterior surface of a respective bone screw arm 14. It is noted, that the sleeve member is somewhat raised with respect to the guide tool body 526, such that the pins 578 are not engaged in the respective pin-receiving bores. Instead, the tips 582 of the pins 578 frictionally engage the surface of the ramp member 568.

Figure 59:
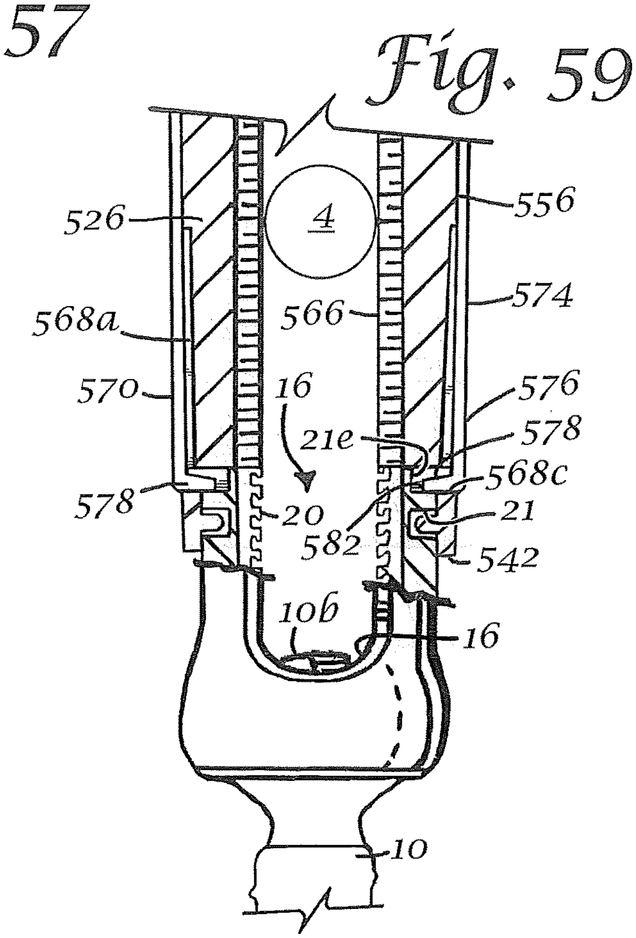
FIG. 59 is an enlarge view of the assembly of FIG. 58 showing the guide tool reversibly attached to the polyaxial bone screw.

To fully engage the guide tool's bone screw attachment structure 568 with the bone screw's tool engagement structure 21, the sleeve member 570 is slidingly moved down the body 526, such that the pins 578 are received into and through the respective pin-receiving bores 568*c*. The pins 578 include a length that is sufficient for them to engage the slots 21 on respective arm top surfaces 15, such as is shown in FIG. 59. When the pins 578 are engaged in the respective slots 21*e*, rotation of the guide tool 500 with respect to the bone screw 6*a* is substantially prevented.

To remove the guide tool 500 from the bone screw 6*a*, the sleeve member 570 is moved axially upward with respect to the body 526, such that the pins 578 are disengaged from the slots 21*e*. As shown in FIG. 59, the pins 578 may be somewhat conically shaped, so as to aid in this disengagement. After the pins 578 and the slots 21*e* have been disengaged, the guide tool body 526 may then be twisted off of the bone screw 6*a*, using a twist-off procedure, such as is described above.

It is to be understood that while certain forms of the present invention have been illustrated and described herein, it is not to be limited to the specific forms or arrangement of parts described and shown.

What is claimed is:

1. A bone anchor comprising:

a receiver and a closure, the receiver attachable with a lower portion of a tool at an inner surface of the tool, the inner surface continuous with a tool channel, the receiver comprising:

a pair of laterally spaced upstanding arms extending about a longitudinal axis of the receiver, the pair of laterally spaced upstanding arms forming a rod-receiving channel therebetween, the rod-receiving channel being closed by the closure, the tool channel being alignable with the receiver channel, each of the laterally spaced upstanding arms comprising:

an external surface extending from a front side to a back side of the receiver;

an upper surface; and a single non-threaded tool engaging laterally opening groove formed on the external surface and extending from at least one of the front side and the back side of the receiver, the laterally opening groove spaced from the upper surface and slanted relative to the longitudinal axis of the receiver, wherein the closure is positionable within the channel when the tool is attached to the laterally opening groove, the tool is attached to the laterally opening groove by twisting the tool to engage the laterally opening groove, and the laterally opening groove is adapted to distally drive the tool during the twisting.

2. The bone anchor of claim 1, wherein the laterally opening groove extends about the external surface from the front side to the back side of the receiver.

3. The bone anchor of claim 2, wherein the laterally opening groove has a vertically extending surface parallel with respect to the longitudinal axis.

4. The bone anchor of claim 2, wherein the laterally opening groove includes a downwardly facing surface perpendicular to the longitudinal axis.

5. The bone anchor of claim 1, wherein the laterally opening groove of a first of the laterally spaced upstanding arms includes a first upper opening at the front side of the receiver and a first lower opening at the back side of the receiver, the first upper opening disposed closer to the upper surface of the first of the laterally spaced upstanding arms.

6. The bone anchor of claim 5, wherein the laterally opening groove of a second of the laterally spaced upstanding arms includes a second upper opening at the back side of the receiver and a second lower opening at the front side of the receiver, the first upper opening disposed closer to the upper surface of the first of the laterally spaced upstanding arms.

7. The bone anchor of claim 5, wherein the laterally opening groove comprises a laterally extending and downwardly directed caming surface.

8. The bone anchor of claim 6, wherein the laterally opening groove further comprises a laterally extending and upwardly directed caming surface disposed opposite the laterally extending and downwardly directed caming surface.

9. The bone anchor of claim 1, wherein the upper surface is adapted to contact a screw abutment surface of the inner surface of the tool when the tool is fully engaged with the laterally opening groove by twisting the tool.

* * * * *